(12) United States Patent
De Fazio et al.

(10) Patent No.: US 8,673,869 B2
(45) Date of Patent: Mar. 18, 2014

(54) DETERMINANTS OF SENSITIVITY TO CHEMOTHERAPEUTIC AGENTS

(75) Inventors: Anna De Fazio, Maroubra (AU); Paul Robert Harnett, Hurstville Grove (AU); Alexander David Guminski, New Farm (AU)

(73) Assignee: Western Sydney Local Health District, Westmead (AU)

( * ) Notice: Subject to any disclaimer, the term of this patent is extended or adjusted under 35 U.S.C. 154(b) by 1246 days.

(21) Appl. No.: 11/793,485

(22) PCT Filed: Dec. 14, 2005

(86) PCT No.: PCT/AU2005/001890
§ 371 (c)(1),
(2), (4) Date: Feb. 24, 2009

(87) PCT Pub. No.: WO2006/063397
PCT Pub. Date: Jun. 22, 2006

(65) Prior Publication Data
US 2009/0203133 A1 Aug. 13, 2009

(30) Foreign Application Priority Data
Dec. 14, 2004 (AU) ................................. 2004907126

(51) Int. Cl.
*C12N 15/11* (2006.01)
*A61K 48/00* (2006.01)
*C07H 21/02* (2006.01)
*C07H 21/04* (2006.01)

(52) U.S. Cl.
USPC ...................................... 514/44 A; 536/24.5

(58) Field of Classification Search
USPC ................... 514/44; 536/23.1, 24.5
See application file for complete search history.

(56) References Cited

U.S. PATENT DOCUMENTS

| 6,660,490 B2 | 12/2003 | Raju | 435/15 |
| 2003/0124609 A1 | 7/2003 | Walker | 435/6 |

FOREIGN PATENT DOCUMENTS

| WO | 01/96375 | 12/2001 |
| WO | 02/03063 | 1/2002 |

OTHER PUBLICATIONS

Liu et al. (Biochemical and Biophysical Research Communications, 2002 vol. 293:1396-1404).*
Hammond et al. (Nature Reviews Genetics 2001, vol. 2:110-119).*
Agarwal et al., "Ovarian Cancer: Strategies for Overcoming Resistance to Chemotherapy," *Nature Rev Cancer* 3:502-516, Jul. 2003.
Baudet, "Another activity for the cardiac biologist: CARP fishing," *Cardiovascular Research* 59:529-531, 2003.
GenBank Accession No. NM_014391, 6 pages, Nov. 14, 2003.
GenBank Accession No. NM_020349, 6 pages, Dec. 12, 2003.

(Continued)

*Primary Examiner* — Terra Cotta Gibbs
(74) *Attorney, Agent, or Firm* — Seed IP Law Group PLLC

(57) ABSTRACT

The present invention provides methods for determining the level of resistance of a tumor cell to one or more chemotherapeutic agents, comprising measuring the level of expression of a muscle ankyrin repeat protein in the tumor cell. The invention also provides methods for increasing the sensitivity of a tumor cell to one or more chemotherapeutic agents, comprising administering to the cell an effective amount of an antagonist of a muscle ankyrin repeat protein. The invention further provides compositions for use in accordance with methods of the invention.

14 Claims, 10 Drawing Sheets

(56) References Cited

OTHER PUBLICATIONS

GenBank Accession No. NM_144994, 5 pages, Mar. 8, 2006.
Kojic et al., "The Ankrd2 Protein, a Link Between the Sarcomere and the Nucleus in Skeletal Muscle," *J. Mo. Biol.* 339:313-325, 2004.
Miller et al., "The Muscle Ankyrin Repeat Proteins: CARP, ankrd2/Arpp and DARP as a Family of Titin Filament-based Stress Response Molecules," *J. Mol. Biol.* 333:951-964, 2003.
Nakada et al., "Cardiac-Restricted Ankyrin-Repeated Protein Is Differentially Induced in Duchenne and Congenital Muscular Dystrophy," *Laboratory Investigation* 83(5):711-719, May 2003.
Segelov et al., "Mechanisms determining sensitivity to cisplatin in three mutant Chinese hamster ovary cell lines," *Mutation Research* 407:243-252, 1998.
Taniguchi et al., "Disruption of the Fanconi anemia-BRCA pathway in cisplatin-sensitive ovarian tumors," *Nature Medicine* 9(5):568-574, May 2003.
Zou et al., "CARP, a cardiac ankyrin repeat protein, is downstream in the *Nkx2-5* homeobox gene pathway," *Development* 124:793-804, 1997.
Komatsu et al., "Copper-transporting P-type adenosine triphosphatase (ATP7B) is associated with cisplatin resistance," *Cancer Research*, 60(5):1312-1316, Mar. 1, 2000.
Nakada et al., "Cardiac-restricted ankyrin-repeated protein is differentially induced in duchenne and congenital muscular dystrophy," *Laboratory Investigation: A Journal of Technical Methods and Pathology*, 83(5): 711-719, May 2003.
Niedner et al., "Identification of genes that mediate sensitivity to cisplatin," *Molecular Pharmacology* 60(6): 1153-1160, Dec. 2001.
Rishi et al., "Identification and characterization of a cell cycle and apoptosis regulatory protein-1 as a novel mediator of apoptosis signaling by retinoid CD437," *Journal of Biological Chemistry*, 278(35): 33422-33435, Aug. 29, 2003.
Scurr et al., "Ankyrin repeat domain 1, ANKRD1, a novel determinant of cisplatin sensitivity expressed in ovarian cancer," *Clinical Cancer Research*, 14(21): 6924-6932, Nov. 1, 2008.
Taniguchi et al., "A human canalicular multispecific organic anion transporter (cMOAT) gene is overexpressed in cisplatin-resistant human cancer cell lines with decreased drug accumulation," *Cancer Research*, 56(18): 4124-4129, Sep. 15, 1996.
Zolk et al., "β-Adrenergic stimulation induces cardiac ankyrin repeat protein expression: Involvement of protein kinase A and calmodulin-dependent kinase," *Cardiovascular Research*, 59(3): 563-572, Sep. 1, 2003.

\* cited by examiner

FIGURE 4A

|  | 241 |  |  |  |  |  | 300 |
|---|---|---|---|---|---|---|---|
| CHO | CEADLNAKDR | EGDTPLHDAV | RLNRYKMIRL | IMTFGADLNT | KNCAGKTPMD | LVLHWQNGTK |  |
| Chicken | CEADLNAKDR | EGDTPMHDAV | RLNRYKMVRL | LILYGADLTI | KNVDGKTPMD | LVIQWQNGTK |  |
| Human | CEADLNAKDR | EGDTPLHDAV | RLNRYKMIRL | LIMYGADLNI | KNCAGKTPMD | LVLHWQNGTK |  |
| Pig | CEADLNAKDR | EGDTPLHDAV | RLNRYKMIRL | LITYGADLNV | KNCAGKTPMD | LVINWQNGTK |  |
| Rabbit | CEADLNAKDR | EGDTPLHDAV | RLNRYKMIRL | LIMYGADLTI | KNSAGKTPMD | LVINWQNGTK |  |
| Rat | CEADLNAKDR | EGDTPLHDAV | RLNRYKMIRL | IMTFGADLNV | KNCAGKTPMI | LVLHWQNGTK |  |
| Consensus | CEADLNAKDR | EGDTPLHDAV | RLNRYKMIRL | LI-YGADLN- | KNCAGKTPMD | LVL-WQNGTK |  |

|  | 301 |  | 319 |
|---|---|---|---|
| CHO | AIFDSLKENG | YKTSRIATF | SEQ ID NO: 15 |
| Chicken | ELFNNLKNNS | YKSAHLNKF | SEQ ID NO: 16 |
| Human | AIFDSLRENS | YKTSRIATF | SEQ ID NO: 17 |
| Pig | AIFDSLKENS | YKASRIATF | SEQ ID NO: 18 |
| Rabbit | AIFDSLKENS | YKTSRIATF | SEQ ID NO: 19 |
| Rat | AIFDSLKENA | YKNSRIATF | SEQ ID NO: 20 |
| Consensus | AIFDSLKENS | YK-SRIATF | SEQ ID NO: 21 |

FIGURE 4B

DETERMINANTS OF SENSITIVITY TO CHEMOTHERAPEUTIC AGENTS

STATEMENT REGARDING SEQUENCE LISTING

The Sequence Listing associated with this application is provided in computer readable form in text format in lieu of a paper copy, and is hereby incorporated by reference into the specification. The name of the computer readable text file containing the Sequence Listing is 880105_401USPCc_SEQUENCE_LISTING.txt. The text file is 30 KB, was created on Aug. 30, 2011, and is being submitted electronically via EFS-Web.

TECHNICAL FIELD

The present invention relates to methods of determining the level of sensitivity or resistance of tumour cells to chemotherapeutic agents, such as platinum-based agents, and thus the responsiveness of patients with tumours to such agents. The invention further relates to methods of reducing resistance (increasing sensitivity) of tumour cells to chemotherapeutic agents and to constructs and compositions for achieving the same.

BACKGROUND OF THE INVENTION

Ovarian cancer is a major contributor to cancer moralities worldwide and is the fifth most common cause of cancer death in Australian women, with approximately 1200 new cases diagnosed and 750 deaths each year (Australian Institute of Health and Welfare, 2002). It is an insidious disease with no specific symptoms and currently no accurate screening test. Consequently, ovarian cancer is usually not diagnosed until extensive spread has occurred. Ovarian cancers show a high response rate to chemotherapy, but unfortunately this does not translate to high cure rates. Indeed, although chemotherapy has increased survival times, there has been little improvement in cure rate, with only 20% of patients with advanced stage ovarian cancer surviving more than 5 years (Kricker, 2002). There is a need for improved therapies for the treatment of advanced ovarian cancer.

Platinum-based drugs including cisplatin and its analogues carboplatin and oxaliplatin, are commonly used chemotherapeutic agents that are effective as single agents or in combination with other drugs in the treatment of a wide variety of malignant solid tumours including germ cell tumours, and cancers arising in lung, upper aero-digestive tract, urothelium as well as the ovarian epithelium. However not all patients respond equally to these drugs (for example approximately 30% of ovarian cancers do not respond) and some patients that do respond to initial treatment subsequently develop resistance to the drugs and do not respond when their disease relapses. Accordingly, there is an urgent need for the development of new therapeutic and management strategies for cancers resistant to chemotherapeutic drugs. Progress in this regard requires improved understanding of the molecular and genetic changes that result in resistance to chemotherapy.

A number of genes have been implicated in resistance to platinum-based chemotherapy. For example demethylation of one of the key genes in the Fanconi anaemia-BRCA1 pathway, FANCF, has been shown to result in increased cisplatin resistance (Taniguchi et al., 2003). At the level of transmembrane transport, there is also evidence that the transmembrane transport protein MRP2, is a platinum export pump and that lack of expression increases platinum sensitivity (Guminski et al., 2005). In addition, the induction of TP53 expression following DNA strand breaks leads to apoptosis and also contributes to cisplatin cytotoxicity (Niedner et al., 2001). However it is not yet possible to predict sensitivity to platinum-based drugs in patients, nor to design rational strategies to overcome resistance. The ability to predict drug response would assist in identifying those patients that fail to respond to therapy without significant benefit, thereby enabling the early selection of a potentially more effective chemotherapy regime. Similarly, a detailed understanding of the pathways involved in the determination of drug sensitivity will lead to novel, targeted strategies for overcoming resistance.

Despite the lack of detailed understanding of the mechanisms that underlie clinical drug tumour resistance, targets have been implicated and clinical trials initiated. These include co-administration of inhibitors of p-glycoprotein and MRP1 drug efflux pumps; however no increase in response rates have been seen in trials conducted thus far. Detailed understanding of the pathways and underlying mechanisms involved in chemotherapeutic response is clearly required to maximize the likelihood of success of these types of approaches.

Further, despite the number of drug-resistance mechanisms that have been described in vitro, to date none of these mechanisms has been shown unequivocally to be important in the clinical setting. This can be attributed to some extent to the models used to study drug resistance. In many studies, sensitive cell lines have been exposed to increasing doses of cytotoxic drugs to generate resistant cell lines and as a consequence cell lines with several-hundred-fold greater resistance to the drug have been generated. However, the clinical relevance of resistance mechanisms generated by such methods has been questioned (Agarwal and Kaye, 2003). In clinical practice, tumours are exposed to repeated fixed drug concentrations and this could select for resistance via different mechanisms. These observations support the need for further searches for genes and pathways that might be clinically useful determinants of tumour response to chemotherapy.

The present invention is predicated on the inventors' finding that the muscle ankyrin repeat protein ANKRD1 (ankyrin repeat domain 1 (cardiac muscle) protein) also known as CARP, is expressed in human ovarian and breast tumours and that alterations in the level of expression of ANKRD1 modulates the sensitivity of the tumour cells to cisplatin.

SUMMARY OF THE INVENTION

According to a first aspect of the present invention there is provided a method for determining the level of resistance of a tumour cell to one or more chemotherapeutic agents, the method comprising measuring the level of expression of a muscle ankyrin repeat protein in the tumour cell.

The muscle ankyrin repeat protein may be selected from the group consisting of ANKRD1, ANKRD2 and ANKRD23.

The muscle ankyrin repeat protein may be ANKRD1 and the ANKRD1 protein may comprise an amino acid sequence as set forth in SEQ ID NO: 1 or SEQ ID NO: 3.

The ANKRD1 protein may be encoded by polynucleotide comprising a nucleic acid sequence as set forth in SEQ ID NO: 2 or SEQ ID NO: 4.

The expression of the muscle ankyrin repeat protein may be determined by measuring protein expression or mRNA expression levels.

The tumour cell may be an ovarian, breast, lung, bladder, testicular, cervical, endometrial or bowel tumour cell or a cell from a head or neck tumour.

The chemotherapeutic agent may be a platinum-based agent, an anthracycline or a taxane. The platinum-based chemotherapeutic agent may be cisplatin or a metabolite, derivative or analogue thereof. The analogue may be carboplatin or oxaliplatin. The anthracycline may be adriamycin or a metabolite, derivative or analogue thereof. The taxane may be paclitaxel, docataxel, or metabolite, derivative or analogue thereof.

According to a second aspect of the present invention there is provided a method of assessing the responsiveness of a patient to one or more chemotherapeutic agents, the method comprising:

(a) obtaining a biological sample containing at least one tumour cell from the patient, and (b) analyzing the level of expression of a muscle ankyrin repeat protein in the at least one tumour cell, wherein the detected level of expression of the muscle ankyrin repeat protein correlates with the sensitivity level of the at least one tumour cell to the chemotherapeutic agent.

The muscle ankyrin repeat protein may be selected from the group consisting of ANKRD1, ANKRD2 and ANKRD23.

The ANKRD1 polypeptide may comprise an amino acid sequence as set forth in SEQ ID NO: 1 or SEQ ID NO: 3.

The ANKRD1 polypeptide may be encoded by polynucleotide comprising a nucleic acid sequence as set forth in SEQ ID NO: 2 or SEQ ID NO: 4.

The expression of the muscle ankyrin repeat protein may be determined by measuring protein expression or mRNA expression levels.

The tumour cell may be an ovarian, breast, lung, bladder, testicular, cervical, endometrial or bowel tumour cell or a cell from a head or neck tumour.

The chemotherapeutic agent may be a platinum-based agent, an anthracycline or a taxane. The platinum-based chemotherapeutic agent may be cisplatin or a metabolite, derivative or analogue thereof. The analogue may be carboplatin or oxaliplatin. The anthracycline may be adriamycin or a metabolite, derivative or analogue thereof. The taxane may be paclitaxel, docataxel, or metabolite, derivative or analogue thereof.

According to a third aspect of the present invention there is provided a method for increasing sensitivity of a tumour cell to one or more chemotherapeutic agents, the method comprising administering to the cell an effective amount of an antagonist of a muscle ankyrin repeat protein.

According to a fourth aspect of the present invention there is provided a method for substantially inhibiting expression of a muscle ankyrin repeat protein in tumour cells, the method comprising introducing into the tumour cells an effective amount of an antagonist of the muscle ankyrin repeat protein.

According to a fifth aspect of the present invention there is provided a composition for increasing sensitivity of a tumour cell to one or more chemotherapeutic agents, the composition comprising an antagonist of a muscle ankyrin repeat protein together with one or more pharmaceutically acceptable carriers, diluents or adjuvants.

According to embodiments of the third, fourth and fifth aspects, the antagonist may be a nucleic acid-based inhibitor, a peptide-based inhibitor or a small molecule inhibitor of the muscle ankyrin repeat protein or polynucleotide encoding the same. The nucleic acid-based inhibitor may be an siRNA molecule or an antisense construct.

The muscle ankyrin repeat protein may be ANKRD1 and the nucleic acid-based inhibitor may be an siRNA molecule. The siRNA molecule may comprise a nucleotide sequence as set forth in any one of SEQ ID NOs:5, 6 or 7, or a fragment thereof.

According to a sixth aspect of the present invention there is provided an isolated inhibitory nucleic acid construct comprising a nucleotide sequence specific to at least a portion of a polynucleotide encoding a muscle ankyrin repeat protein, wherein the nucleic acid construct substantially inhibits expression of the muscle ankyrin repeat protein in tumour cells.

The portion of the polynucleotide may include the coding region of the gene encoding the muscle ankyrin repeat protein and/or one or more regulatory regions of the gene.

The inhibitory nucleic acid construct may be located in a vector. The vector may direct transcription of the construct.

The inhibitory nucleic acid construct may be an siRNA molecule.

In one embodiment, the muscle ankyrin repeat protein is ANKRD1 and the nucleotide sequence of the siRNA molecule comprises:

(a) the nucleotide sequence set forth in any one of SEQ ID NOs:5, 6 or 7, or a fragment thereof; or (b) a nucleotide sequence having at least 85% identity to the nucleotide sequence set forth in any one of SEQ ID NOs: 5, 6 or 7, or fragment thereof.

In other embodiments the nucleotide sequence may have at least 85%, at least 90% identity, or at least 95% identity, to the nucleotide sequence set forth in any one of SEQ ID NOs: 5, 6 or 7, or fragment thereof.

According to a seventh aspect of the present invention there is provided a method for substantially inhibiting expression of a muscle ankyrin repeat protein in tumour cells, the method comprising introducing into the tumour cells an effective amount of an inhibitory nucleic acid construct according to the sixth aspect.

According to an eighth aspect of the present invention there is provided a method for increasing sensitivity of tumour cells to one or more chemotherapeutic agents, the method comprising introducing into the tumour cells an effective amount of an inhibitory nucleic acid construct according to the sixth aspect.

According to a ninth aspect of the present invention there is provided a composition for use in the method of the seventh or eighth aspects, the composition comprising an inhibitory nucleic acid construct according to the sixth aspect.

The composition may further comprise one or more chemotherapeutic agents. The composition may further comprise one or more pharmaceutically acceptable carriers, diluents or adjuvants.

Definitions

In the context of this specification, the term "comprising" means "including principally, but not necessarily solely". Furthermore, variations of the word "comprising", such as "comprise" and "comprises", have correspondingly varied meanings.

The term "polynucleotide" as used herein refers to a single- or double-stranded polymer of deoxyribonucleotide, ribonucleotide bases or known analogues of natural nucleotides, or mixtures thereof. The term includes reference to the specified sequence as well as to the sequence complimentary thereto, unless otherwise indicated.

The term "polypeptide" means a polymer made up of amino acids linked together by peptide bonds. The terms "polypeptide" and "protein" are used interchangeably herein, although for the purposes of the present invention a "polypeptide" may constitute a portion of a full length protein.

As used herein the term "effective amount" includes within its meaning a non-toxic but sufficient amount of an antisense construct to provide the desired effect. The exact amount required will vary depending on factors such as the level of expression of muscle ankyrin repeat protein in the absence of the construct, the type of tumour to be treated, the severity of the tumour, the drug resistance level of the tumour, the species being treated, the age and general condition of the subject, the particular construct being administered, the mode of administration and so forth. Thus, it is not possible to specify an exact "effective amount". However, for any given case, an appropriate "effective amount" may be determined by one of ordinary skill in the art using only routine experimentation.

In the context of this specification, the term "antagonist" refers to any agent capable of inhibiting the expression or activity of a protein, polypeptide portion thereof, or polynucleotide. Thus, the antagonist may operate to prevent transcription, translation, post-transcriptional or post-translational processing or otherwise inhibit the activity of the protein, polypeptide or polynucleotide in any way, via either direct or indirect action. The antagonist may for example be nucleic acid, peptide, any other suitable chemical compound or molecule or any combination of these. Additionally, it will be understood that in indirectly impairing the activity of the protein, polypeptide or polynucleotide, the antagonist may affect the activity of other cellular molecules which may in turn act as regulators of the protein, polypeptide or polynucleotide itself. Similarly, the antagonist may affect the activity of molecules which are themselves subject to regulation or modulation by the protein, polypeptide or polynucleotide.

The term "inhibiting" as used herein as it pertains to expression or activity of a muscle ankyrin repeat protein or polynucleotide encoding the same does not necessarily mean completely inhibiting expression. Rather, expression of the protein, polypeptide or polynucleotide is inhibited to an extent, and/or for a time, sufficient to produce the desired effect.

The term "expression" as used herein refers interchangeably to expression of a polypeptide or protein and expression of a polynucleotide or gene. Expression of a polynucleotide may be determined, for example, by measuring the production of messenger RNA (mRNA) transcript levels. Expression of a protein or polypeptide may be determined, for example, by immunoassay using an antibody(ies) that bind with the polypeptide.

In the context of this specification, the term "activity" as it pertains to a protein, polypeptide or polynucleotide means any cellular function, action, effect or influence exerted by the protein, polypeptide or polynucleotide, either by a nucleic acid sequence or fragment thereof, or by the protein or polypeptide itself or any fragment thereof.

In the context of this specification, the term "specific" when used in relation to the nucleotide sequence of an inhibitory nucleic acid construct of the invention means substantially specific, but not necessarily exclusively so. For example, the nucleotide sequence of an inhibitory nucleic acid construct according to the present invention may display less than 100% sequence identity with one particular muscle ankyrin repeat protein-encoding polynucleotide and retain specificity thereto.

BRIEF DESCRIPTION OF THE DRAWINGS

The present invention will now be described, by way of example only, with reference to the following drawings:

FIGS. 4A-4B. Amino acid sequence alignment of the Hamster (CHO-K1) ANKRD1 gene product with chicken, human, pig, rabbit and rat ANKRD1 sequences. Identical amino acids are shaded black, similar amino acids are shaded grey and unique amino acids are unshaded. The consensus amino acid sequence is also shown. Sequence analysis conducted using GCG Eclustalw and Prettybox programs via the Australian National Genomic Information Service (ANGIS).

Figure 1:
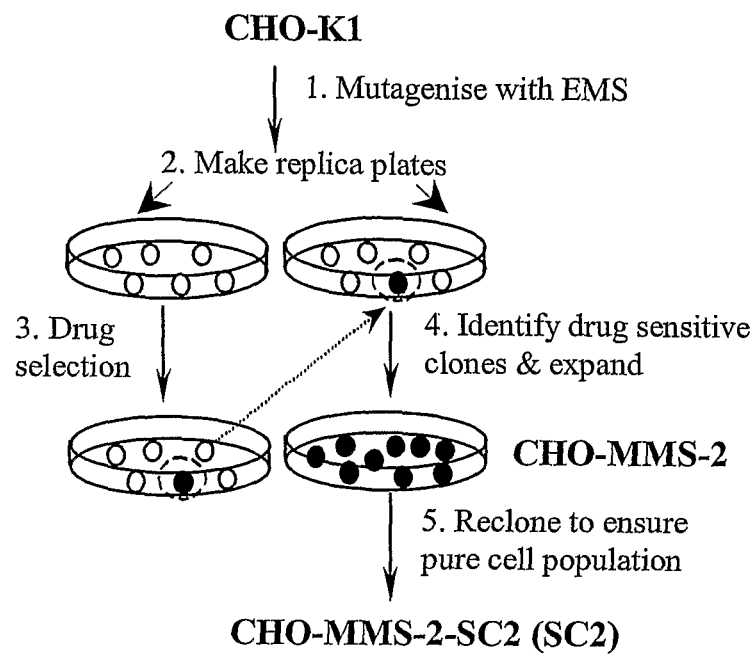
FIG. 1 is a schematic illustration of the derivation of cell line models according to the present invention. Mutations were induced in the parental CHO-K1 cell line by treatment with the chemical mutagen, ethyl methane sulfonate (EMS). Mutant clones with increased sensitivity to cisplatin were identified. One of these mutants (MMS-2) was chosen for further characterization and was sub-cloned to ensure a pure, clonal population (CHO-K1-MMS-2-SC2 referred to as SC2 cells).

The amino acid sequence set forth in SEQ ID NO:1 is the amino acid sequence of the human ANKRD1 protein, deposited under GenBank database accession number NM_014391.

The nucleotide sequence set forth in SEQ ID NO:2 is the nucleotide sequence of the gene encoding the human ANKRD1 protein, deposited under GenBank database accession number NM_014391.

The amino acid sequence set forth in SEQ ID NO:3 is the amino acid sequence of the ANKRD1 protein from the Chinese Hamster Ovary cell line CHO-K1.

The nucleotide sequence set forth in SEQ ID NO:4 is the nucleotide sequence of the gene encoding the ANKRD1 protein from the Chinese Hamster Ovary cell line CHO-K1.

The nucleotide sequences set forth in SEQ ID NOs:5 to 7 are nucleotide sequences of the siRNA molecules, siRNA41, siRNA58 and siRNA77 respectively, as disclosed herein.

BEST MODE OF PERFORMING THE INVENTION

The present inventors have used a unique cell line model and stringent differential display strategy to identify gene determinants of platinum-based drug sensitivity. The inventors' utilized a cell line model where random mutagenesis was used to create clones that are exquisitely sensitive to platinum-based therapy. In this model, neither the parent cell line (which is intrinsically platinum-resistant) nor the sensitive clones have ever been exposed to chemotherapeutic drugs. Thus, rather than seeking to identify genes associated with resistance, the approach has been to identify gene determinants of drug sensitivity—as the ultimate clinical goal is to increase the sensitivity of tumors to chemotherapeutic agents. One of the genes identified by this strategy encodes ankyrin repeat domain 1 (cardiac muscle) protein (ANKRD1), also known as cardiac ankyrin repeat protein (CARP) and cardiac adriamycin-responsive protein. ANKRD1 is also homologous to the human protein C-193 (cytokine inducible nuclear protein). ANKRD1 belongs to a family of structurally related proteins with conserved biological function known as muscle ankyrin repeat proteins (MARPs), the known members of which currently include ANKRD1, ANKRD2 (also known as Arpp) and ANKRD23 (also known as DARP (diabetes-related ankyrin repeat protein)) (see Miller et al., 2003; Kojic et al., 2004). Each of these three proteins contains an N-terminally-located nuclear localization signal and four C-terminal ankyrin repeat motifs of 33 amino acid residues, the second of which represents a distinct subclass (Miller et al., 2003). The term MARP is used herein to refer, collectively, to the family of muscle ankyrin repeat proteins exemplified by ANKRD1 (CARP), ANKRD2/Arpp and ANKRD23 (DARP).

The ANKRD1 gene encodes a nuclear co-repressor for cardiac gene expression; it is downstream of the cardiac homeobox gene, Nkx 2.5 and is an early marker of the cardiac muscle lineage. ANKRD1 represses muscle-specific promoters in cardiomyocytes, interacting with the transcription factor YB1 and repressing expression of the ventricular isoform of myosin light chain 2, a trial natriuretic factor, and cardiac troponin C genes. It is developmentally downregulated in cardiac tissue and is re-expressed in several cardiac pathologies including cardiac hypertrophy (Baudet, 2003). ANKRD1 is also induced in regenerating myofibers of patients with Duchenne muscular dystrophy (Nakada et al., 2003). ANKRD1 is most abundant in the heart but it is also found in skeletal muscle, lung, liver, kidney, prostate and endothelial cells (Nakada et al., 2003; Zou et al., 1997; Chu et al., 1995).

As disclosed herein the present inventors have now found that ANKRD1 is expressed in normal human ovarian epithelial cells, in ovarian and breast cancer cell lines and ovarian tumour specimens. ANKRD1 was however found to be barely detectable in a mutated ovarian cell line (SC2) with unusual sensitivity to cisplatin. In addition gene transfection and gene knock-down experiments (siRNA) revealed that cisplatin cytotoxicity could be altered by changing ANKRD1 expression levels. These results indicate that ANKRD1, or a molecular pathway involving ANKRD1, has a direct pro-survival effect following exposure to cisplatin. Neither ANKRD1 nor its homologues have previously been associated with ovarian cancer or response to platinum therapy.

Accordingly, one aspect of the present invention provides a method for determining the level of sensitivity/resistance of a tumour cell to one or more chemotherapeutic agents, the method comprising measuring the level or expression of a muscle ankyrin repeat protein in the tumour cell. The invention also provides a method for assessing the responsiveness of a patient to one or more chemotherapeutic agents. Further, another aspect of the invention provides a method for increasing sensitivity of a tumour cell to one or more chemotherapeutic agents, the method comprising administering to the cell an effective amount of an antagonist of a muscle ankyrin repeat protein.

Although exemplified herein in relation to the muscle ankyrin repeat protein ANKRD1, those skilled in the art will readily appreciate that the present invention is not so limited and extends to other members, both known and yet to be elucidated, of the family of related muscle ankyrin repeat proteins, including but not limited to ANKRD2/Arpp and ANKRD23 (DARP).

Muscle Ankyrin Repeat Proteins and Expression Thereof

Typically the polypeptides of and polynucleotides encoding muscle ankyrin repeat proteins (MARPs) to which the methods and compositions of the present invention relate are the human protein and gene. The amino acid sequence of the human ANKRD1 protein is shown in SEQ ID NO:1 (GenBank Accession No. NM_014391), and the nucleotide sequence of the human ANKRD1 gene is shown in SEQ ID NO:2 (GenBank Accession No. NM_014391). Also disclosed herein are the CHO ANKRD1 protein and nucleotide sequences, set forth in SEQ ID NOs: 3 and 4, respectively. The nucleotide and polypeptide sequences of human ANKRD2/Arpp are found under GenBank Accession No. NM_020349, and the nucleotide and polypeptide sequences of human ANKRD23 (DARP) are found under GenBank Accession No. NM_144994.

According to embodiments of the invention, the ANKRD1 polypeptide may have the amino sequence as set forth in SEQ ID NO:1 or 3 or display sufficient sequence identity thereto to hybridise to the sequence of SEQ ID NO:1 or 3. In alternative embodiments, the nucleotide sequence of the polynucleotide may share at least 50%, 60%, 70%, 80%, 85%, 90%, 96%, 97%, 98% or 99% identity with the sequence set forth in SEQ ID NO:3.

According to embodiments of the invention, the ANKRD1 polynucleotide may have the nucleotide sequence as set forth in SEQ ID NO:2 or 4 or display sufficient sequence identity thereto to hybridise to the sequence of SEQ ID NO:2 or 4. In alternative embodiments, the nucleotide sequence of the polynucleotide may share at least 30%, 40%, 50%, 60%, 70%, 80%, 85%, 90%, 96%, 97%, 98% or 99% identity with the sequence set forth in SEQ ID NO:2 or 4.

Within the scope of the terms "protein", "polypeptide" and "polynucleotide" as used herein are fragments and variants thereof.

The term "fragment" refers to a nucleic acid or polypeptide sequence that encodes a constituent or is a constituent of a full-length MARP protein. In terms of the polypeptide the fragment possesses qualitative biological activity in common with the full-length protein.

The term "variant" as used herein refers to substantially similar sequences. Generally, nucleic acid sequence variants encode polypeptides which possess qualitative biological activity in common. Generally, polypeptide sequence variants also possess qualitative biological activity in common. Further, these polypeptide sequence variants may share at least 50%, 55%, 60%, 65%, 70%, 75%, 80%, 85%, 90%, 95%, 96%, 97%, 98% or 99% sequence identity.

Further, a variant polypeptide may include analogues, wherein the term "analogue" means a polypeptide which is a derivative of a MARP, which derivative comprises addition, deletion, substitution of one or more amino acids, such that the polypeptide retains substantially the same function as the native MARP from which it is derived. The term "conservative amino acid substitution" refers to a substitution or replacement of one amino acid for another amino acid with similar properties within a polypeptide chain (primary sequence of a protein). For example, the substitution of the charged amino acid glutamic acid (Glu) for the similarly charged amino acid aspartic acid (Asp) would be a conservative amino acid substitution.

Expression of polynucleotides, proteins or polypeptides may be determined by any one of a number of techniques well known to those skilled in the art. For example, expression may be determined by assaying mRNA transcript abundance in a sample. mRNA abundance may be measured, for example, by reverse transcriptase-PCR. Alternatively expression of a protein or polypeptide may be determined using an antibody that binds to the protein or polypeptide or a fragment thereof, using a technique such as enzyme-linked immunosorbent assay (ELISA).

Antagonists

Embodiments of the present invention provide methods and compositions for inhibiting the expression of a MARP using an antagonist thereof. Typically the antagonist may be nucleic-acid based, peptide-based or other suitable chemical compound.

In particular embodiments the antagonist is a nucleic-acid based inhibitor of expression of polynucleotide encoding a MARP or a fragment thereof. Suitable molecules include small interfering RNA (siRNA) species, antisense constructs, such as antisense oligonucleotides, and catalytic antisense nucleic acid constructs. Suitable molecules can be manufactured by chemical synthesis, recombinant DNA procedures or, in the case of antisense RNA, by transcription in vitro or in vivo when linked to a promoter, by methods known to those skilled in the art.

One suitable technology for inhibiting gene expression, known as RNA interference (RNAi), (see, eg. Chuang et al. (2000) *PNAS USA* 97: 4985) may be used for the purposes of the present invention, according to known methods in the art (for example Fire et al. (1998) *Nature* 391: 806-811; Hammond, et al. (2001) *Nature Rev. Genet.* 2: 110-1119; Hammond et al., (2000) *Nature* 404: 293-296; Bernstein et al. (2001) *Nature* 409: 363-366; Elbashir et al (2001) *Nature* 411: 494-498; WO 99/49029 and WO 01/70949, the disclosures of which are incorporated herein by reference), to inhibit the expression of MARPs. RNAi refers to a means of selective post-transcriptional gene silencing by destruction of specific mRNA by small interfering RNA molecules (siRNA). The siRNA is typically generated by cleavage of double stranded RNA, where one strand is identical to the message to be inactivated. Double-stranded RNA molecules may be synthesised in which one strand is identical to a specific region of the mRNA transcript of the MARP of interest and introduced directly. Alternatively corresponding dsDNA can be employed, which, once presented intracellularly is converted into dsRNA. Methods for the synthesis of suitable siRNA molecules for use in RNAi and for achieving post-transcriptional gene silencing are known to those of skill in the art. The skilled addressee will appreciate that a range of suitable siRNA constructs capable of inhibiting the expression of a MARP can be identified and generated based on knowledge of the sequence of the gene in question using routine procedures known to those skilled in the art without undue experimentation.

Those skilled in the art will appreciate that there need not necessarily be 100% nucleotide sequence match between the target sequence and the siRNA sequence. The capacity for mismatch therebetween is dependent largely on the location of the mismatch within the sequences. In some instances, mismatches of 2 or 3 nucleotide may be acceptable but in other instances a single nucleotide mismatch is enough to negate the effectiveness of the siRNA. The suitability of a particular siRNA molecule may be determined using routine procedures known to those skilled in the art without undue experimentation. By way of example, the nucleotide sequences of exemplary siRNA molecules for the inhibition of ANKRD1 are set forth in any one of SEQ ID NOs:5, 6 or 7. Suitable siRNA molecules may display at least 80% sequence identity to the sequences set forth in SEQ ID NOs: 5, 6 or 7.

In alternative embodiments, the nucleotide sequence of the siRNA molecule may share at least 85%, at least 90%, or at least 95% identity with the sequence set forth in any one of SEQ ID NOs:5, 6 or 7. Those skilled in the art will appreciate that one or base substitutions, additions or deletions of these sequences may be made in generating a sequence of at least 80% nucleotide sequence identity, at least 85% nucleotide sequence identity, at least 90% nucleotide sequence identity or at least 95% nucleotide sequence identity. Further, the skilled addressee will appreciate that a number of other suitable siRNA constructs capable of inhibiting the expression of ANKRD1 can be identified and generated using routine procedures known to those skilled in the art without undue experimentation.

Sequences of antisense constructs of the invention may be derived from various regions of a MARP gene. Antisense constructs may be designed to target and bind to regulatory regions of the nucleotide sequence or to coding (exon) or non-coding (intron) sequences. Antisense constructs of the invention may be generated which are at least substantially complementary across their length to a region of the gene in question. Binding of an antisense construct to its complementary cellular sequence may interfere with transcription, RNA processing, transport, translation and/or mRNA stability.

Antisense constructs of the present invention may be derived from the human MARP gene, or non-human animal variants thereof. For example, antisense constructs derived from non-human genes having at least 50% sequence identity with the human gene and can be used in the methods of the invention for administration to tumours of humans and/or non-human animals, Non-human MARP genes may have at least 60%, at least 70%, at least 80% or at least 90% sequence identity with their human homologue.

Suitable antisense oligonucleotides may be prepared by methods well known to those of skill in the art. Typically antisense oligonucleotides will be synthesized on automated synthesizers. Suitable antisense oligonucleotides may include modifications designed to improve their delivery into cells, their stability once inside a cell, and/or their binding to the appropriate target. For example, the antisense oligonucleotide may be modified by the addition of one or more phosphorothioate linkages, or the inclusion of one or morpholine rings into the backbone.

In particular embodiments of the invention suitable inhibitory nucleic acid molecules may be administered to the tumour cells in a vector. The vector may be a plasmid vector, a viral vector, or any other suitable vehicle adapted for the insertion and foreign sequences and introduction into eukaryotic cells. Preferably the vector is an expression vector capable of directing the transcription of the DNA sequence of an inhibitory nucleic acid molecule of the invention into RNA. Viral expression vectors include, for example, epstein-barr virus-, bovine papilloma virus-, adenovirus- and adeno-associated virus-based vectors. In one embodiment, the vector is episomal. The use of a suitable episomal vector provides a means of maintaining the inhibitory nucleic acid molecule in the tumour cells in high copy number extra-chromosomally thereby eliminating potential effects of chromosomal integration.

A further means of substantially inhibiting MARP gene expression may be achieved by introducing catalytic antisense nucleic acid constructs, such as ribozymes, which are capable of cleaving RNA transcripts and thereby preventing the production of wildtype protein. Ribozymes are targeted to and anneal with a particular sequence by virtue of two regions of sequence complementarity to the target flanking the ribozyme catalytic site. After binding the ribozyme cleaves the target in a site-specific manner. The design and testing of ribozymes which specifically recognize and cleave MARP sequences can be achieved by techniques well known to those in the art (for example Lieber and Strauss, (1995) *Mol. Cell. Biol.* 15:540-551, the disclosure of which is incorporated herein by reference).

Alternative antagonists of MARPs may include antibodies. Suitable antibodies include, but are not limited to polyclonal antibodies, monoclonal antibodies, chimeric antibodies, humanized antibodies, single chain antibodies and Fab fragments.

Antibodies may be prepared from discrete regions or fragments of the polypeptide of interest. An antigenic polypeptide contains at least about 5, and preferably at least about 10, amino acids. Methods for the generation of suitable antibodies will be readily appreciated by those skilled in the art. For example, a suitable monoclonal antibody, typically containing Fab portions, may be prepared using the hybridoma technology described in *Antibodies-A Laboratory Manual*, Harlow and Lane, eds. Cold Spring Harbor Laboratory, N.Y. (1988), the disclosure of which is incorporated herein by reference.

Similarly, there are various procedures known in the art which may be used for the production of polyclonal antibodies to polypeptides of interest as disclosed herein. For the production of polyclonal antibodies, various host animals, including but not limited to rabbits, mice, rats, sheep, goats, etc, can be immunized by injection with a polypeptide, or fragment or analogue thereof. Further, the polypeptide or fragment or analogue thereof can be conjugated to an immunogenic carrier, e.g., bovine serum albumin (BSA) or keyhole limpet hemocyanin (KLH). Also, various adjuvants may be used to increase the immunological response, including but not limited to Freund's (complete and incomplete), mineral gels such as aluminium hydroxide, surface active substances such as lysolecithin, pluronic polyols, polyanions, peptides, oil emulsions, keyhole limpet hemocyanins, dinitrophenol, and potentially useful human adjuvants such as BCG (*Bacillus Calmette-Guerin*) and *Corynebacterium parvum*.

Screening for the desired antibody can also be accomplished by a variety of techniques known in the art. Assays for immunospecific binding of antibodies may include, but are not limited to, radioimmunoassays, ELISAs (enzyme-linked immunosorbent assay), sandwich immunoassays, immunoradiometric assays, gel diffusion precipitation reactions, immunodiffusion assays, in situ immunoassays, Western blots, precipitation reactions, agglutination assays, complement fixation assays, immunofluorescence assays, protein A assays, and immunoelectrophoresis assays, and the like (see, for example, Ausubel et al., eds, 1994, *Current Protocols in Molecular Biology*, Vol. 1, John Wiley & Sons, Inc., New York). Antibody binding may be detected by virtue of a detectable label on the primary antibody. Alternatively, the primary antibody may be detected by virtue of its binding with a secondary antibody or reagent which is appropriately labelled. A variety of methods are known in the art for detecting binding in an immunoassay and are within the scope of the present invention.

Also included within the scope of the present invention are alternative forms of inhibition of MARP expression, including, for example, small molecule or other non-nucleic acid or non-proteinaceous inhibitors. Such inhibitors may be identified by those skilled in the art by screening using routine techniques.

Chemotherapeutic Agents

According to methods of the invention, antisense constructs of the invention and other antagonists may be employed to increase the sensitivity (decrease the resistance) of tumour cells to chemotherapeutic agents, such as platinum-based agents, anthracyclines and taxanes. Platinum-based agents include those agents which inhibit tumour cell growth by binding to DNA and inducing DNA damage. Several numbers of platinum-based drugs have been used as chemotherapeutic agents. For the purposes of the present invention, examples of such drugs include, but are not limited to, cisplatin and metabolites, derivatives or analogues thereof. Such derivatives and analogues include carboplatin and oxaliplatin. Exemplary anthracyclines include adriamycin and metabolites, derivatives and analogues thereof. Exemplary taxanes include paclitaxel, docataxel, and metabolites, derivatives and analogues thereof.

Those skilled in the art will appreciate that the chemotherapeutic agents to which the present invention refers are not limited to the above-mentioned specific agents but include any compound suitable for chemotherapeutic use.

Tumours

Embodiments of the present invention provide methods for the determination and the alteration of levels of resistance/sensitivity of tumour cells to chemotherapeutic agents, predicated on the inventors' finding of ANKRD1 expression in human ovarian and breast tumours and of modulation in the sensitivity of tumour cells to cisplatin in response to modulation of the expression of ANKRD1. Accordingly the methods and compositions of the present invention relate to the analysis and treatment of a variety of tumour cell types, depending on the nature of the chemotherapeutic agent the resistance to which assessment or alteration is desired. For example in the case of platinum-based chemotherapeutic agents, the tumour cells may be ovarian, breast, lung, bladder, testicular, cervical, endometrial or bowel tumour cells or cells from a head or neck tumour.

Methods of Treatment

Embodiments of the present invention relate to the use of antagonists of the invention in methods and compositions for treating individuals having cancer, the individual either being in need of or undergoing platinum-based chemotherapy. Accordingly, the present invention contemplates the administration of antagonists of the invention to such individuals having cancer in order to inhibit ANKRD1 expression thereby increasing sensitivity of the cancer cells to one or more platinum-based chemotherapeutic agents. Accordingly, antagonists of the invention may be administered in combination therapy with such platinum-based chemotherapeutic agents. For such combination therapies, each component of the combination therapy may be administered at the same time, or sequentially in any order, or at different times, so as to provide the desired therapeutic effect. One or more suitable antagonist may be combined with one or more suitable platinum-based chemotherapeutic agent in a single composition, optionally also comprising one or more pharmaceutically acceptable carriers, diluents or adjuvants.

It will be understood that the specific dose level of a composition of the invention for any particular individual will depend upon a variety of factors including, for example, the activity of the specific antagonists and/or platinum-based chemotherapeutic agents employed, the age, body weight, general health and diet of the individual to be treated, the time of administration, rate of excretion, and combination with any other treatment or therapy. Single or multiple administrations can be carried out with dose levels and pattern being selected by the treating physician.

Examples of pharmaceutically acceptable carriers or diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

The compositions of the invention may be in a form suitable for parenteral administration, or in the form of a formulation suitable for oral ingestion (such as capsules, tablets, caplets, elixirs, for example).

For administration as an injectable solution or suspension, non-toxic parenterally acceptable diluents or carriers can include, Ringer's solution, isotonic saline, phosphate buffered saline, ethanol and 1,2 propylene glycol.

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl distearate which delay disintegration.

Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

The emulsions for oral administration may further comprise one or more emulsifying agents. Suitable emulsifying agents include dispersing agents as exemplified above or natural gums such as guar gum, gum acacia or gum tragacanth.

Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference herein.

The composition may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

The compositions may also be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolizable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which are incorporated herein by reference.

The present invention will now be further described in greater detail by reference to the following specific examples, which should not be construed as in any way limiting the scope of the invention.

EXAMPLES

Example 1

Cell Line Model of Platinum Sensitivity

Figure 2:
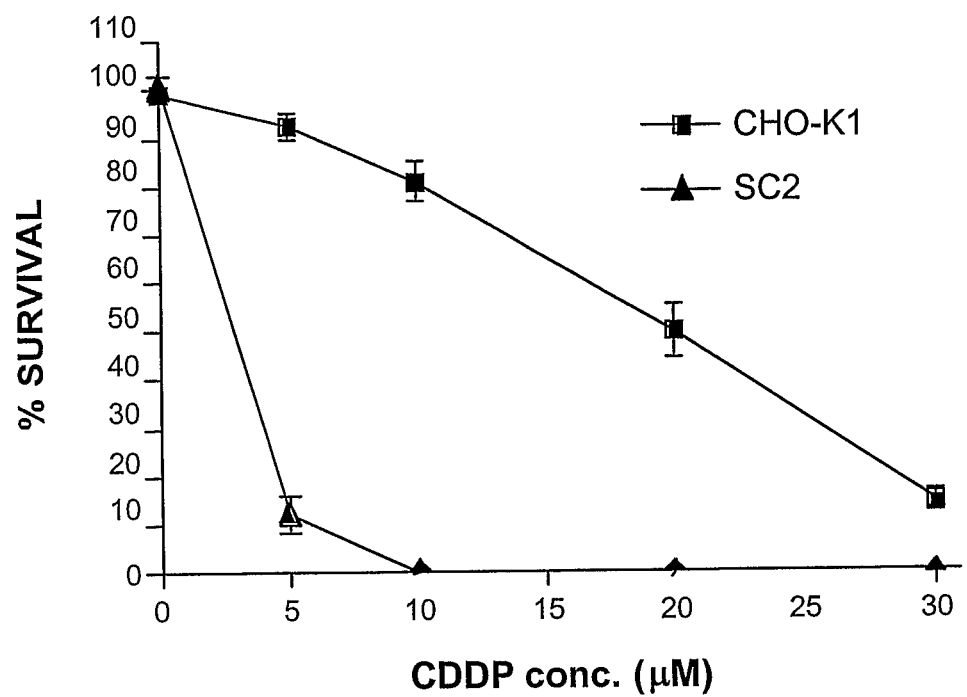
FIG. 2. Cisplatin sensitivity of CHO cell lines. Parental CHO-K1 and the platinum-sensitive clone SC2 were exposed to a range of cisplatin (CDDP) concentrations for 2 hrs. The drug was then removed and the surviving cell fraction was determined by colony formation over 6 days. Colonies were fixed, stained with 0.1% crystal violet and counted. The results are expressed as a percentage of vehicle-treated control (mean and standard error from duplicate plates in at least three separate experiments) at differing cisplatin (CDDP) concentrations.

The present inventors have used a novel approach to identify genes that determine sensitivity to platinum-based chemotherapeutic agents. This strategy utilized the mutant Chinese hamster ovary (CHO) cell line SC2 which is more sensitive to platinum than the parent CHO-K1 cell line. Parental CHO-K1 and mutant CHO cell lines were provided as a gift from Dr I Hickson and Dr C Robson (Imperial Cancer Research Fund, Oxford UK) (Robson, C, et al, 1985). The strategy adopted is outlined in FIG. 1. CHO-K1 cells were mutagenised with ethyl methane sulphonate (EMS). Mutants with altered sensitivity to cisplatin were isolated using replica plating. Colonies were grown in agar then transferred onto replica plates—untreated or drug selection plates. Clones growing on untreated but not drug treated plates were isolated and characterized. One exquisitely cisplatin-sensitive mutant, MMS-2, was utilized for further analysis and was subcloned to ensure a pure clonal population of cells (CHO-K1-MMS-2-SC2, referred to herein as SC2 cells). Parental CHO-K1 and the platinum-sensitive clone SC2 were exposed to a range of cisplatin concentrations for 2 hrs. The drug was then removed and the surviving cell fraction was determined by colony formation over 6 days. Colonies were fixed, stained with 0.1% crystal violet and counted. Exposure to 10 uM cisplatin for 2 hr results in less than 2% cell survival of SC2 cells, compared with greater than 80% survival in CHO-K1 cells (see FIG. 2). The mechanisms underlying cisplatin sensitivity in this mutant were then investigated and at least two defects related to cisplatin response, increased drug influx and defective DNA repair, were identified (Segelov, E. et al, 1998).

Example 2

Identification of a New Regulator of Platinum Sensitivity

A stringent differential display PCR strategy was used to isolate differentially expressed genes in the pair of CHO lines with differing platinum sensitivity, CHO-K1 and SC2.

RNA was extracted from CHO-K1 cells, SC2 cells and a partial revertant (10C5) for comparison.

Differential display-PCR (DD-PCR) was used to examine differential gene expression between CHO K1 and SC2 cells. RNA was extracted from exponentially growing early passage cells. Primer sets for differential display were obtained commercially (Genomyx, Foster City, Calif., USA). Reverse transcription (RT) was performed using a DD anchor primer (final concentration 2 µM) and 2 µl of RNA from each clone freshly diluted to a concentration of 100 ng/µl. The reaction mix included dNTP mix (final concentration 25 µM each), DTT (final concentration 10 mM), RNase inhibitor (final concentration 1 U/µl, RNasin, Promega, Madison, Wis., USA), RT enzyme (final concentration 2 U/µl, Superscript II Life Technologies, Gibco BRL, Grand Island, N.Y., USA), RT enzyme buffer (1×) and sterile water to 20 µl. Negative controls lacking either RT enzyme or RNA template were performed as was a positive control using HeLa RNA supplied by the manufacturer (Genomyx). The RT reaction was performed in a hot lid thermal cycler (Hybaid, Integrated Sciences, Willoughby, NSW, Australia) and conditions were 25° for 10 min, 42° C. for 60 min, 70° C. for 15 min then 4° C.

RT products were either used immediately or stored at −20° C. PCR mix consisted of 3' anchor primer and 5' arbitrary primer (final concentration 0.2 µM each, Genomyx), dNTP mix (final concentration 20 µM each, Genomyx), PCR buffer (final concentration 1×), α[$^{33}$P]dATP (final concentration 0.125 µCi/µl), Taq polymerase (final concentration 0.05 units/µl, AmpliTaq, Perkin Elmer, N.J., USA), 2 µl RT product and DNase free water to 20 µl. PCR cycling parameters were: 95° C. for 2 min; 92° C. for 15 sec, 46° C. for 30 sec, 72° C. for 2 min (four cycles); 92° C. for 15 sec, 60° C. for 30 sec, 72° C. for 2 min (25 cycles); and extension at 72° C. for 7 min.

DD-PCR products were resolved on a 6% denaturing polyacrylamide gel. To reduce the risk of false negatives independent, duplicate harvests of RNA were performed from the CHO clones to be compared and the RT-PCR reaction was performed in duplicate on each of these harvests. Thus for each anchor primer/arbitrary primer combination, a total of 4 lanes for each clone were run on a gel. Bands were only selected if the difference between clones was consistent across at least 3 out of the 4 replicates.

Differential display analysis revealed 28 differentially expressed bands confirmed on duplicate RNA samples. The selected bands were cut from the dried polyacrylamide gel, amplified by PCR, isolated by cloning into a bacterial vector (pGEMT-Easy Cloning Kit; Promega) and sequenced using an ABI automated sequencer (PE Applied Biosystems, Foster City, Calif., USA). All sequence searches were performed using data and tools available at ANGIS (Australian National Genomic Information Service, (http:///www dot angis dot org dot au) and the NCBI website (http:///www dot ncbi dot nlm nih dot gov/). Four genes were confirmed to be consistently altered in either the sensitive or resistance cell lines and their identity revealed by sequence analysis. These genes and their expression relative to cisplatin resistance are indicated in Table 1 below.

TABLE 1

| GENE | DIRECTION OF CHANGE | FOLD CHANGE[a] |
|---|---|---|
| Ribosomal protein L19 | Increased in resistant cells | 2x |
| Cardiac adriamycin response protein (ANKRD1) | Increased in resistant cells | 9.3x |
| Ribosomal protein L39 | Decreased in resistant cells | 2x |
| EST 251111[b] | Decreased in resistant cells | 1.7x |

[a]Determined by Northern Blot Analysis or Real-time quantitative PCR
[b]Bcr/Abl regulated protein One of the differentially expressed genes was found to be homologous to ANKRD1 (cardiac ankyrin repeat protein (Zou et al. 1997); known also as cardiac adriamycin-responsive protein (Jeyaseelan et al., 1997) and homologous to the human gene, C-193 (Chu et al., 1995).

Expression of ANKRD1 in CHO-K1 and SC2 cells was determined by Northern blot analysis. Total RNA was isolated by lysis in guanidinium isothiocyanate solution followed by CsCl centrifugation using standard methods (Sambrook et al., 1989) or by using Tri-reagent according to manufacturer's instructions (Sigma Aldrich, Steinheim, Germany) and Northern blot analysis was performed by standard techniques. An oligonucleotide probe to ANKRD1 was designed from common sequence of the published human, rat and mouse ANKRD1 cDNA (5'-GTC CAG GGG TTC AGC CAC AA-3'; SEQ ID NO:8). An oligonucleotide designed to the 18S rRNA sequence (5'-ACG GTA TCT GAT CGT CTT CGA ACC-3'; SEQ ID NO:9) was used to control for equal loading and transfer on Northern blots.

Probes were end-labeled with $(\gamma$-$^{32}$P) ATP (5,000 Ci/mmol) using T4 polynucleotide enzyme (Promega) and unincorporated label was removed using G25 Sephadex spin column. Following hybridisation the filters were washed then exposed to either radiographic film (BioMax, Eastman Kodak, Rochester, N.Y., USA) or a phosphoimager screen (Molecular Dynamics, Sunnyvale, Calif., USA). Lane intensity was compared using the Image Quant program (Molecular Dynamics). Filters were then stripped and reprobed for 18S.

Figure 3:
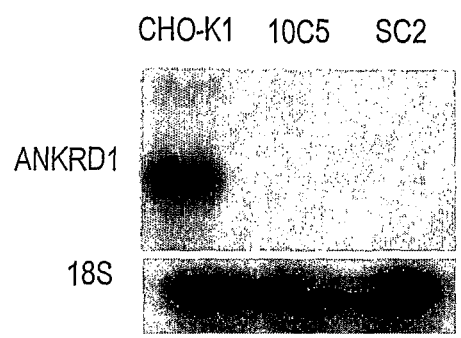
FIG. 3. Expression of ANKRD1 in CHO-K1 cells, cisplatin sensitive (SC2) CHO cells and 10C5 cells with intermediate cisplatin sensitivity by Northern blot. The blot was also probed for 18S RNA as a control for RNA loading and transfer.

By Northern blotting ANKRD1 was confirmed to be expressed in CHO-K1 and to be undetectable in SC2 cells (FIG. 3). By real-time PCR (see Example 6) ANKRD1 expression was found to be 9.3 fold higher in the parental cell line (0.185 ng in CHO-K1 compared to 0.02 ng in SC2) (Table 1).

Figure 4A:
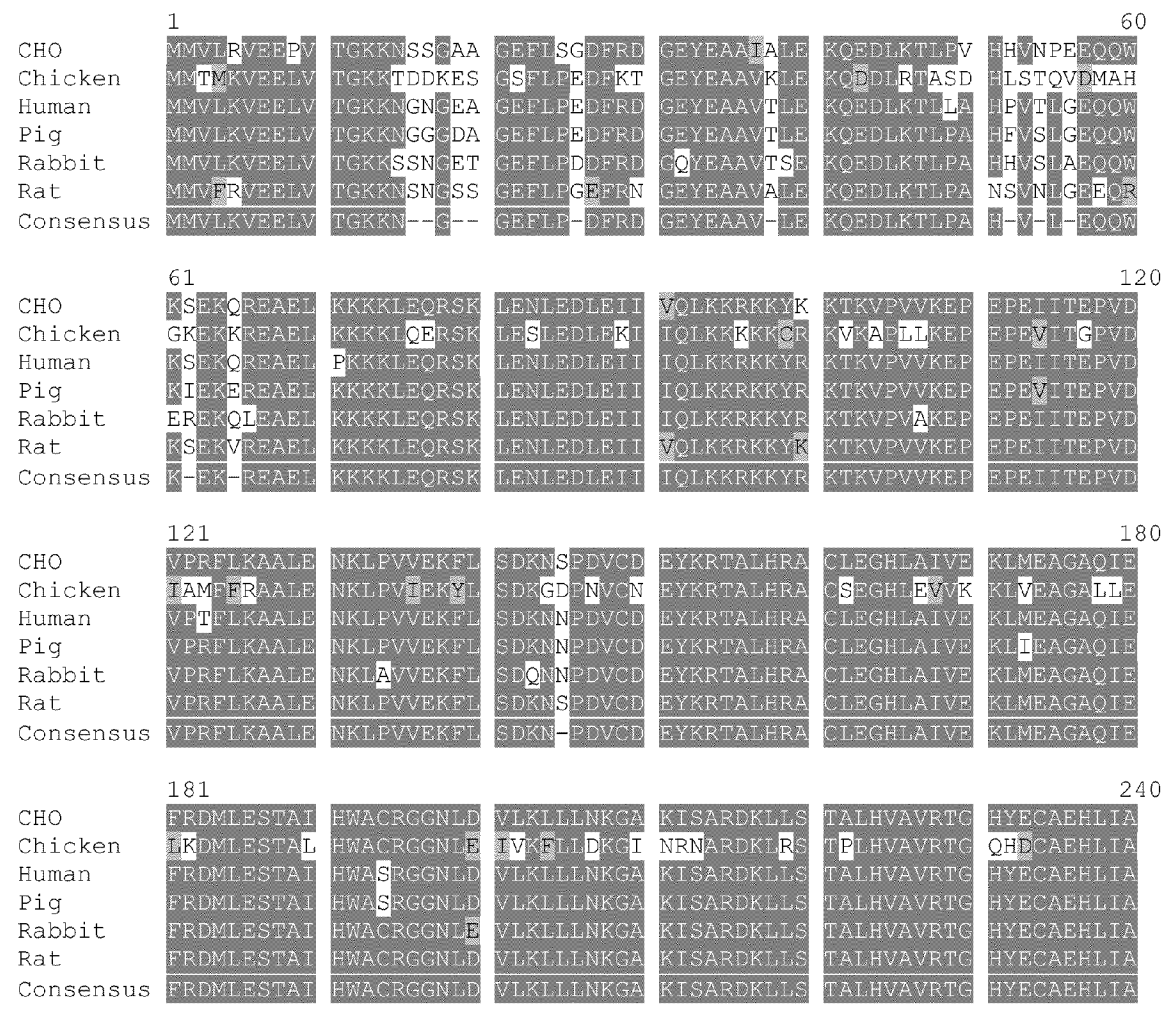

The full length ANKRD1 gene from CHO-K1 was sequenced. The full-length open reading frame was obtained using the SMART™ 5'-; 3'-RACE cDNA Amplification kit (BD Biosciences Clontech, Palo Alto, Calif., USA). RACE was carried out according to the manufacturer's protocol. The two initial primers, forward 5'-AAC ATG ATG GTG CTG AGA GTA GAG GAG CCG-3' (SEQ ID NO:10) and reverse 5'-GCA CCA TCA TGT TGG CAG CAG TGA GTC T-3' (SEQ ID NO:11), were designed from the sequence isolated from the DD-PCR. An additional internal primer was required to obtain the full-length sequence, 5'-TGC GCT GGA GAA CAA ACT GCC AGT TG-3' (SEQ ID NO:12) at position 383 bp (primers synthesized by Sigma Genosys, Castle Hill, NSW, Australia). The full-length sequence was then compared to all known ANKRD1 genes using multisequence analysis programs available at ANGIS. This analysis revealed a 957 bp open reading frame with high homology to ANKRD1 in other species; amino acid identities of 91.2%, 93.4%, 91.8% to human, mouse, and rat sequences respectively (see FIG. 4).

Example 3

Increased Expression of ANKRD1 Decreases Cisplatin Sensitivity

Figure 5:
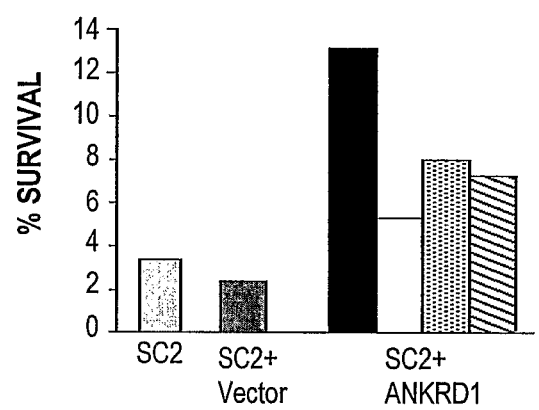
FIG. 5. Increased resistance of SC2 cells to cisplatin following transfection with ANKRD1. Rat ANKRD1 cDNA was transfected into SC2 cells and transfected clones selected. ANKRD1-transfected clones were exposed to 6 µM cisplatin and the surviving fraction was measured by clonogenic assay. Survival in 4 transfected clones (SC2+ANKRD1) was compared with untransfected SC2 cells and empty vector-control transfected SC2 cells (SC2+vector).

To determine whether ANKRD1 has the ability to decrease sensitivity to cisplatin, rat ANKRD1 cDNA in the pcDNA3.1 expression vector, under the control of a CMV promoter, (a gift from the laboratory of Prof. L. Kedes, University of Southern California, USA) was transfected into the ANKRD1-deficient, platinum-sensitive SC2 mutant using Lipofectamine 2000 (Invitrogen Life Technologies, Carlsbad, Calif., USA). Transfected clones were selected and maintained in 400 µg/ml G-418 (Gibco-BRL). ANKRD1 transfection resulted in increased resistance to cisplatin (FIG. 5), providing evidence that ANKRD1 may play a role in modulating sensitivity to cisplatin.

Example 4

Decreased Expression of ANKRD1 Increases Cisplatin Sensitivity

To confirm that ANKRD1 was able to modulate platinum sensitivity, the converse hypothesis was tested, that decreasing ANKRD1 expression in the resistant, CHO-K1 cell line would increase sensitivity. Three 19 bp siRNA oligonucleotides were designed to regions encoding the N- and C-terminus as well as to a central portion of the coding region of the CHO ANKRD1 sequence. The sequences of the sense strands of these siRNA oligonucleotides are shown in SEQ ID NOs: 5 (siRNA41), 6 (siRNA58) and 7 (siRNA77). These siRNA oligonucleotides were designed so as to also allow targeting to the human ANKRD1 sequence Hairpin siRNA encoding DNA oligonucleotide insert sequences were cloned into the pSilencer™ 2.1-U6 hygro vector (Ambion, Austin, Tex., USA) and transfected into CHO-K1 using Lipofectamine 2000. Transfected cells were selected and maintained in 500 µg/mL hygromycin B (Invitrogen). Additionally, a silencing negative control pSilencer vector supplied by the manufacturer expressing an siRNA (siN9) with low homology to any known sequences in the human, mouse, and rat genomes, was also stably expressed in CHO-K1 cells.

Figure 6A:
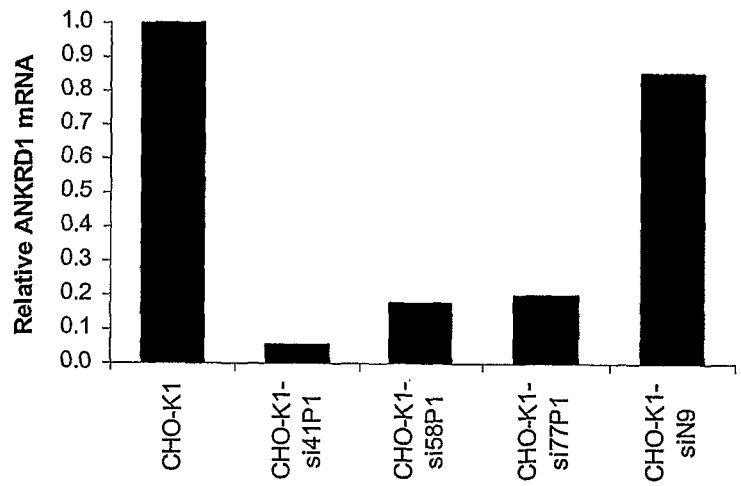
FIG. 6. Increased sensitivity to cisplatin in CHO-K1 cells following reduction of ANKRD1 expression by siRNA. CHO-K1 were transfected with one of three inserts designed to knock-down ANKRD1 expression by targeting regions of the open reading frame encoding the N-terminus (siRNA41; SEQ ID NO: 5), the central portion (siRNA58; SEQ ID NO: 6) or the C-terminus (siRNA77; SEQ ID NO: 7). Pools (P1) of siRNA transfected cells were selected and maintained in hygromycin B. A. ANKRD1 mRNA was measured by real-time PCR. Results are shown as a percentage of the parent CHO-K1 ANKRD1 mRNA levels and corrected for rodent GAPDH (glyceraldehyde-3-phosphate dehydrogenase) and 18S rRNA. B. Cisplatin (CDDP) sensitivity in CHO-K1 and siRNA transfected cells was measured by clonogenic assay. The results are expressed as the mean and standard error of duplicate plates from at least three separate experiments.

As shown in FIG. 6A, ANKRD1 expression was virtually ablated in the cells transfected with ANKRD1 siRNA41 (SEQ ID NO:5), targeting the region encoding the N-terminus. ANKRD1 expression was similarly reduced in cells expressing siRNA58 (SEQ ID NO:6) and siRNA77 (SEQ ID NO:7). The negative control (siN9) had minimal effect on ANKRD1 expression.

Figure 6B:
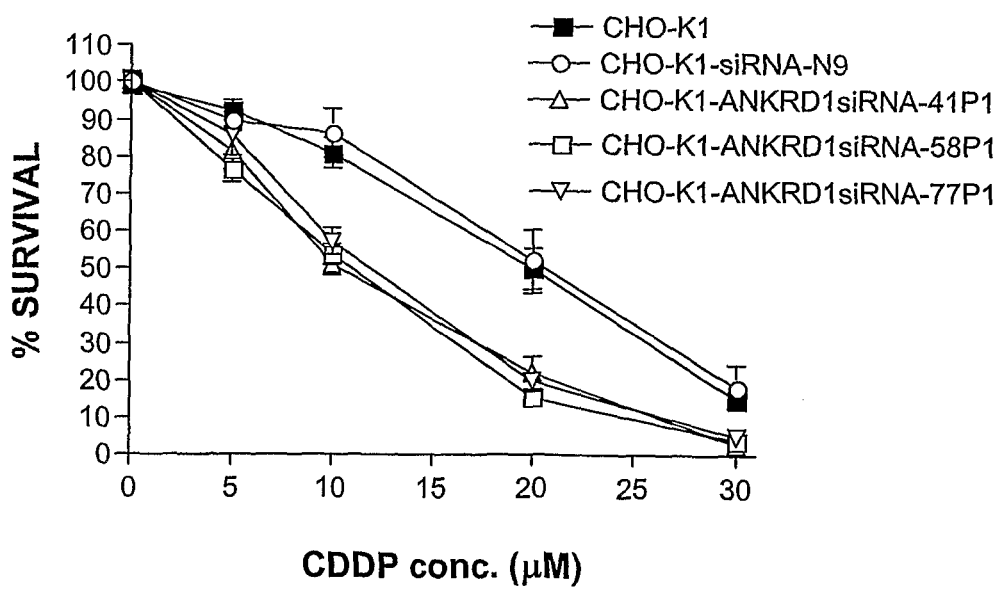

Cisplatin sensitivity was determined in the pools of ANKRD1 siRNA transfectants. siRNA-mediated reduction in ANKRD1 expression resulted in a significant decrease in resistance to cisplatin (FIG. 6B), with the 2-fold reduction in $IC_{50}$ compared with vector-transfected controls. No significant difference in increased sensitivity to cisplatin was observed between the siRNAs targeting different regions of the ANKRD1 gene. This data confirmed that alteration in ANKRD1 expression was able to alter sensitivity to cisplatin in CHO cells.

Example 5

Detection of ANKRD1 in Human Ovarian Tumours

The inventors measured ANKRD1 mRNA levels by real-time PCR (see Example 6) in a cohort of 64 serous ovarian adenocarcinomas (approved by the Institutional Human Research Ethics Committee). The majority were of moderate or high grade (low n=1, moderate n=28, high n=34, unknown n=1), and from patients with advanced stage disease (stage I n=2, stage II n=1, stage III n=56, stage IV n=5, determined in accordance with FIGO criteria). These patients reflect the most common epithelial ovarian cases treated with platinum-based chemotherapy. The tissue specimens examined came from patients treated between 1988 and 2002 in the Department of Gynecological Oncology at Westmead Hospital. Tissue examined was excised at the time of primary surgery, prior to the administration of chemotherapy in all but one case. Tissues were snap-frozen and stored in liquid nitrogen in the Department of Gynecological Oncology tissue bank. Cases were selected according the tumor histological type indicated by original pathology reports, and only cases of serous adenocarcinoma were included.

For each case, RNA was extracted from cryosections or pieces of snap frozen tumor specimens and an adjacent haematoxylin and eosin stained section was taken to verify tissue content. Total RNA was isolated from frozen sections using the Absolutely RNA Microprep kit (Stratagene, LaJolla, Calif., USA) following homogenisation with a hand operated pestle grinder in the lysis buffer provided; or from pulverized frozen tissue pieces by lysis in guanidinium isothiocyanate solution followed by CsCl centrifugation using standard methods. RNA quality was assessed using an Agilent 2100 Bioanalyser and RNA Integrity Number software (Agilent Technologies, Palo Alto, Calif., USA). ANKRD1 mRNA levels were measured by real-time PCR and analysis was performed on coded samples with the operator blinded to all clinical data. ANKRD1 mRNA was relatively low, or absent, in 72% of cases (46/64) and moderate or relatively high expression was seen in 28% of cases (18/64). The level of ANKRD1 expression was significantly associated with overall survival (p=0.03, Cox Regression Analysis), patients with a high tumor level of ANKRD1 having a significantly poorer outcome compared with patients whose tumors had low ANKRD1 expression. Multivariate analysis indicated that the relationship between ANKRD1 level and overall survival was independent of the extent of residual disease following debulking laparotomy and patient age at diagnosis.

Example 6

ANKRD1 Expression in Human Ovarian and Breast Cell Lines

ANKRD1 expression has not previously been reported in ovarian epithelial cells. In the present study ANKRD1 mRNA levels were measured in 16 human ovarian and breast cell lines by real-time PCR. Total RNA was isolated by lysis in guanidinium isothiocyanate solution followed by CsCl centrifugation using standard methods (see for example Sambrook, J., et al 1989, and Wilson in *Current Protocols in Molecular Biology* (Ausubel, F. M. et al. Eds.) Greene Publishing Associated and Wiley-Interscience, NY 1994) or by Stratagene Absolutely RNA Microprep Kit used according to manufacturer's protocol. RNA was reverse transcribed into cDNA using Superscript III First Strand Synthesis System (Invitrogen) according to manufacturer's instructions, in a final volume of 20 µL.

To examine ANKRD1 mRNA expression, 100 ng of cDNA used as templates in real-time PCR using the ABI PRISM 7700 Sequence Detection System (PE Applied Biosystems). Samples were made up in a final volume of 25 µL with Platinum Quantitative PCR Supermix-UDG (Invitrogen) and 250 nM of each primer set. The amplification conditions were 50° C. for 2 min, 95° C. for 10 min then 50 cycles of 95° C. for 15 sec and 60° C. for 60 sec. Relative concentrations of ANKRD1 and housekeeping genes were determined by comparison of Ct values to a standard curve produced using a sample containing cDNA produced from RNA of known concentration. Primers for ANKRD1 were designed using the LUX™ primer design software (Invitrogen), labelled with FAM and were: 5'-GM CCT TCG GCA CAT CCA CAG GTC-FAM (sense) (SEQ ID NO:13) and 5'-AGA AAC AGC GAG AGG CAG AGC (antisense) (SEQ ID NO:14). Equal cDNA concentrations were confirmed using commercially available primer and probe sets for two housekeeping genes, the VIC-labelled 18S and human P0 PDARs (Applied Biosystems).

Figure 7:
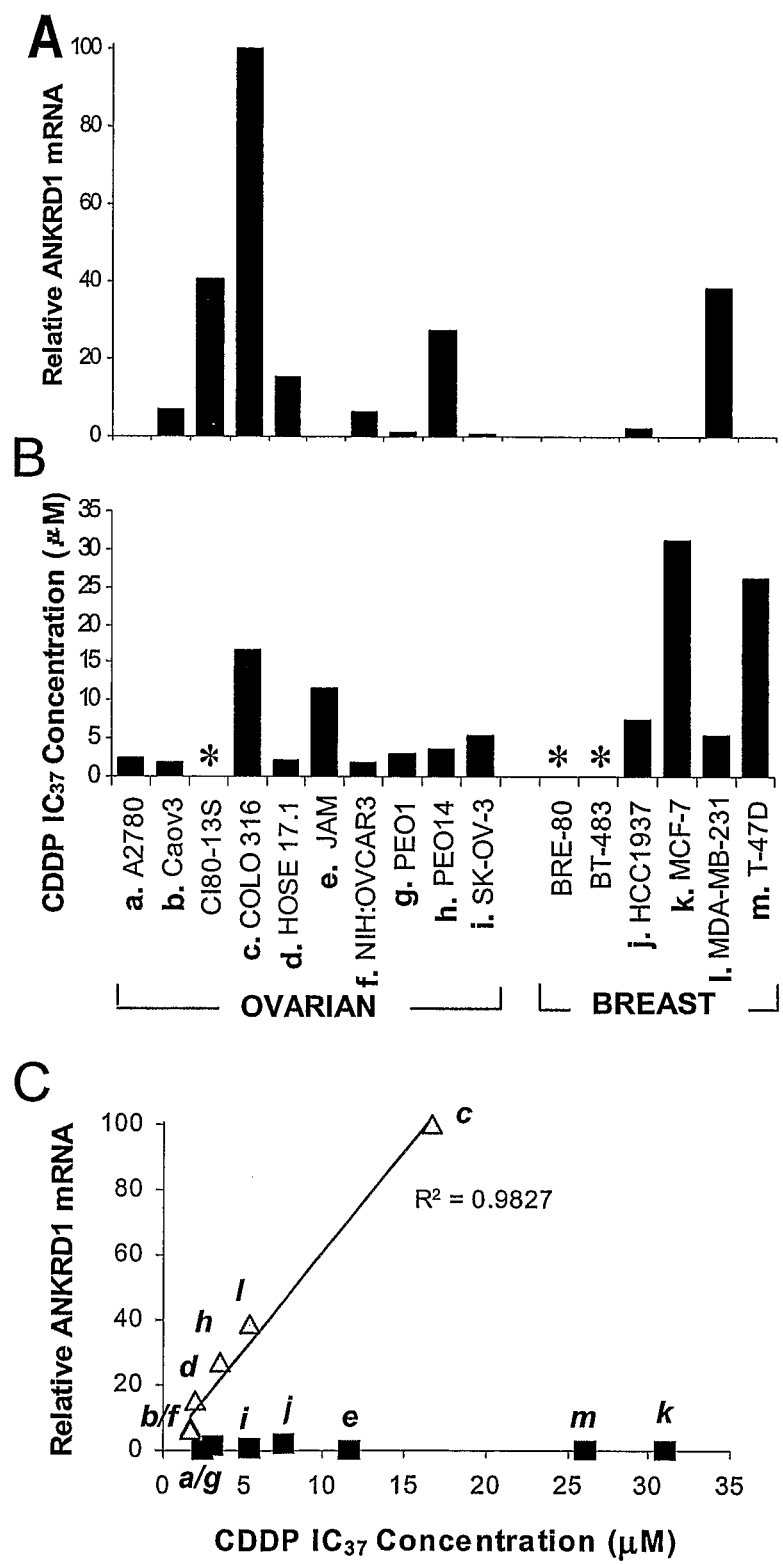
FIG. 7. Expression of ANKRD1 in ovarian and breast cell lines. RNA was extracted from a range of normal and malignant ovarian and breast cell lines. ANKRD1 expression was measured by real-time PCR. A. Results are shown as relative mRNA levels, corrected for human P0 (acidic phosphoprotein P0; also known as 36B4, part of the 60S ribosomal RNA complex) and 18S rRNA. All cell lines are human. HOSE 17.1 and BRE-80 are normal ovarian and breast cell lines respectively; the remaining cell lines are malignant. B. Cisplatin (CDDP) sensitivity was determined for 13 of the cell lines. Survival was determined by MTS assay after exposing the cells to drug for 72 hr. The $IC_{37}$ is shown for each cell line, results are the mean determined from between two and seven independent experiments. Asterix indicates $IC_{37}$ not determined. C. Association between growth inhibition by cisplatin ($IC_{37}$) and expression of ANKRD1 mRNA in 13 cell lines. Regression analysis was performed on cell lines expressing detectable levels of ANKRD1 (triangles; $R^2=0.9827$, Linear Regression Analysis) and did not include cell lines with ANKRD1 levels at or below the level of detection (closed squares).

As shown in FIG. 7A ANKRD1 expression was detected at moderate to high levels in 5/9 ovarian cancer cell lines as well as in the normal ovarian cell line HOSE 17.1 and in 1/5 breast cancer cell lines, with little detectable expression in the normal breast cell line BRE-80. Moreover a greater than 1000-fold difference in the level of expression in the ovarian cancer cell lines was observed, with very high expression in COLO 316 and Caov-3, moderate expression in PE01 and low expression in JAM, SK-OV-3 and A2780.

Relative cisplatin sensitivity was measured in 13 cell lines using a colorimetric proliferation assay. Cells were seeded into 96-well plates in a volume of 100 µl at 500 to 2000 cells per well. The following day 50 µl of complete medium containing concentrations of cisplatin ranging from 625 nM to 20 µM were added to duplicate wells and MTS assays (based on color conversion by viable cells MTS, 3-(4,5-dimethylthiazol-2-yl)-5-(3-carboxymethoxyphenyl)-2-(4-sulphenyl)-2H-terazolium, inner salt) were carried out as described by the manufacturer (Promega) on the day of seeding and subsequently at days 1, 2, 3, 4 and 6 post-drug exposure. $IC_{37}$ values were calculated for each cell line from survival curves, using data generated from between two to seven independent experiments.

As depicted in FIG. 7B, a range of response was observed, with COLO 316, T-47D and MCF-7 being among the most resistant cell lines and HOSE 17.1, A2780 and PEO1, amongst the most sensitive. When the relative levels of ANKRD1 mRNA were compared with the $IC_{37}$ for cisplatin, the cell lines clearly separated into two groups. In one group of six cell lines (COLO 316, MDA-MB-231, PEO14, HOSE 17.1, NIH:OVCAR3 and Caov3) a linear relationship between ANKRD1 levels and platinum response was observed ($R^2$=0.9827; Linear Regression Analysis). The second group of cell lines (HCC1937, A2780, PEO1, T-47D, SK-OV-3, JAM, MCF-7) did not express ANKRD1, and consequently there was no relationship with the $IC_{37}$ for cisplatin. No highly platinum-sensitive cell lines were found to express appreciable levels of ANKRD1 (FIG. 7C) which may indicate that high levels of ANKRD1 are not compatible with a high level of sensitivity to cisplatin, further supporting our hypothesis that ANKRD1 plays an important role in determining response to cisplatin.

Example 7

Association Between Clinical Chemo-Sensitivity and ANKRD1 Expression in Human Ovarian Tumours To determine whether ANKRD1 expression is associated with sensitivity to platinum-based chemotherapy in ovarian cancer, a rare subgroup of ovarian carcinoma patients (n=3) with extreme sensitivity to chemotherapy were selected. These patients were diagnosed with Stage III, serous ovarian carcinoma and had macroscopic disease remaining following debulking surgery i.e. these cases were similar to the majority of cases of epithelial ovarian cancer, however the patients were classified as chemo-sensitive as the tumour did not recur following primary treatment and overall survival was greater than 4 years in all cases. This included 2 patients who remained disease free after minimum follow-up of 10 years (Table 2). These cases were compared with a group that were chemo-resistant (n=5) ie patients with evidence of disease progression during primary platinum-based therapy (persistent elevation of the serum tumour marker CA125, and/or increasing disease measured by imaging or palpation) with a correspondingly short median survival (approx 1 year) (Table 2). The two subgroups were from the extreme ends of the spectrum of clinical outcome but were not significantly different in respect of features that have been associated with clinical outcome in ovarian cancer, including surgical stage, extent of residual disease following debulking surgery, patient age or tumour grade (Table 2).

Patients were identified retrospectively from hospital records and were women diagnosed with primary carcinoma of the ovary or peritoneum. Clinical and pathological features are summarized in Table 2. In all cases the histological tumour type was serous or papillary serous adenocarcinoma.

Patients were treated by surgery, and adjuvant chemotherapy according to standard protocols specifying cisplatin or carboplatin, usually in combination with cyclophosphamide or paclitaxel. In the majority of cases, tumour examined was excised at the time of primary surgery, prior to the administration of chemotherapy. One patient who had tumour excised post-platinum based chemotherapy were also examined.

Details of tumour histological type and grade were derived from original pathology reports and the research protocol was approved by the Human Research Ethics Committee, Westmead Hospital, NSW, Australia. Tumour specimens were snap frozen and stored cryogenically in the Westmead Hospital Gynecological Oncology Tumour Bank. Total RNA was isolated from pulverized frozen sections/pieces by lysis in guanidinium isothiocyanate solution followed by CsCl centrifugation using standard methods. ANKRD1 mRNA levels were measured by real-time PCR and analysis was performed on coded samples with the operator blinded to all clinical data.

Figure 8:
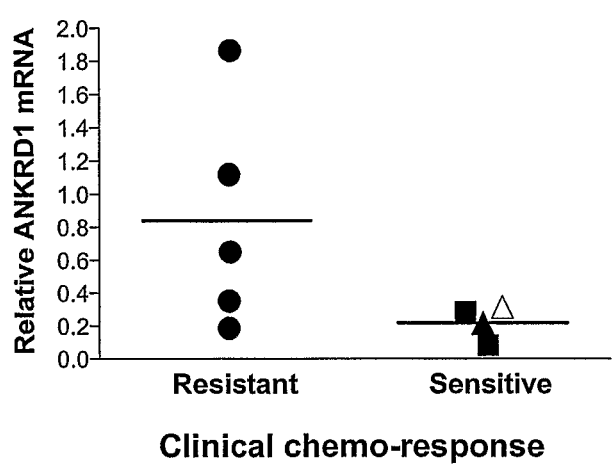
FIG. 8. Expression of ANKRD1 in human ovarian tumours and association with response to chemotherapy. Two subgroups of ovarian carcinoma patients were selected from the extreme ends of the spectrum of clinical outcome. Cases were designated 'chemo-sensitive' if the patient had a sustained response to therapy (>4 years) and 'chemo-resistant' if the tumour progressed while the patient was on primary platinum-based treatment. The two cohorts were not different with respect to other clinical features known to be associated with patient outcome such as surgical stage and extent of residual disease following debulking surgery (Table 2). RNA was extracted from frozen ovarian tumour specimens. In one patient (number 146) RNA was extracted from tissue collected from two anatomical sites, the primary ovarian tumour and a metastasis to the momentum. ANKRD1 expression was measured by real-time PCR and results are shown as relative mRNA levels, corrected for human P0 and 18S rRNA. The ANKRD1 mRNA levels for case 146 are represented by triangles, where the filled triangle represents the primary tumour and the open triangle represents the metastasis. Samples from the other two patients in the chemo-sensitive cohort are represented by filled squares, and filled circles represent the samples from the chemo-resistant patients.

ANKRD1 mRNA was detected in all tumours examined (8/8, 100%) with a greater than 50-fold difference in the level of expression found between the tumours. Expression of ANKRD1 mRNA was low in all cases (3/3, 100%) that were classified as chemo-sensitive (FIG. 8) and did not differ between the primary tumour and a metastasis in the one case examined. ANKRD1 expression was higher in 3/5 chemo-resistant cases, compared with the chemo-sensitive cases, and a wide range of ANKRD1 expression was found in this group. This data is highly consistent with the data from earlier examples that low ANKRD1 expression is indicative of sensitivity to platinum-based chemotherapy.

Example 8

ANKRD1 Expression and Sensitivity to Cisplatin Analogues

Carboplatin is a cisplatin analogue with a similar pattern of activity to cisplatin, with reduced neuro- and nephrotoxicity. Oxaliplatin is an analogue with activity against colorectal carcinomas (unlike cisplatin) and appears to have greater activity in vitro against tumour cells that have acquired DNA mismatch repair deficiencies. In the present study the inventors compared the response to carboplatin and oxaliplatin in the 2 CHO cell lines with differing ANKRD1 expression: the CHO-K1 parental line, with high ANKRD1 gene expression, and the SC2 cells, with very low ANKRD1 gene expression.

CHO-K1 and SC2 cells were each seeded into 24-well plates, incubated overnight then exposed to a range of con-

TABLE 2

Clinical and histopathological characteristics of ovarian cancer cohort. (Cases are grouped according to clinical response to platinum-based chemotherapy)

| Clinical Response | Patient Number | Patient Age | Tumour Grade | FIGO Stage | Residual disease | Progression-free survival (weeks) | Overall survival (weeks) |
|---|---|---|---|---|---|---|---|
| Chemo-sensitive | 83A | 67 | 3 | III | <1 cm | 674[a] | 674[a] |
|  | 351A | 52 | 3 | III | >2 cm | 243[a] | 243[a] |
|  | 146B, C[d] | 55 | 4 | III | >2 cm | 553[a] | 553[a] |
| Chemo-resistant | 117A | 31 | 1 | III | >2 cm | n/a[b] | 60 |
|  | 224B[c] | 48 | 3 | III | >2 cm | n/a[b] | 53 |
|  | 261A | 55 | 3 | III | >2 cm | n/a[b] | 58 |
|  | 317A | 62 | 2 | III | >2 cm | n/a[b] | 54 |
|  | 380A | 65 | 2 | IV | <1 cm | n/a[b] | 53 |

[a]Censored (ie. the patient had not relapsed (progression-free survival) or died (overall survival) before completion of the study)
[b]Not applicable as disease progression was evident during primary treatment
[c]Patient received 1 cycle of carboplatin/cyclophosphamide prior to surgery.
[d]RNA was extracted from tissue collected from the primary tumour site (B) and from the metastasis to the omentum (C).

centrations of carboplatin or oxaliplatin for 2 hr. The drugs were removed, wells washed and the growth media replaced. Cells were incubated for 6 days and cell proliferation measured using a modified colorimetric MTS (3-(4,5-dimethylthiazol-2-yl)-5-(3-carboxy-methoxyphenyl)-2-(4-sulfophenyl)-2H-tetrazolium, inner salt) proliferation assay. MTS solution was added to each well and colour development measured on a plate reader at 490 nm.

Figure 9:
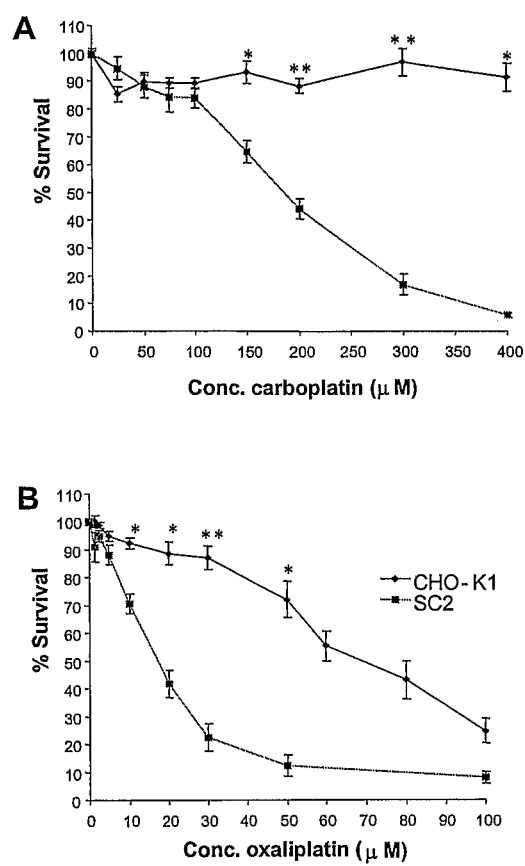
FIG. 9. Effect of carboplatin (A) and oxaliplatin (B) on cell survival in CHO-K1 cells (diamonds) and SC2 cells (squares). Cell survival was measured by modified MTS assay. Results are expressed as a percentage of the vehicle-treated control, as a mean and standard error of triplicate wells from six independent experiments. Results were subjected to a paired t-test where * is $p<0.05$ and ** is $p<0.005$.

FIG. 9 demonstrates that CHO-K1 cells are significantly more resistant to both carboplatin and oxaliplatin compared to the SC2 cells. This differential response to carboplatin and oxaliplatin is very similar to that observed with the parent compound, cisplatin, tested in the same CHO cell lines with differing levels of ANKRD1 expression. These results suggest that ANKRD1 expression may be associated with response to platinum-based agents in general.

REFERENCES

Agarwal, R and Kaye, S B, Ovarian cancer: Strategies for overcoming resistance to chemotherapy. *Nature Rev Cancer* 3: 502-16, 2003.

Australian Institute of Health and Welfare and Australian Association of Cancer Registries. Cancer in Australia 1999. AIHW, Can berra, 2002.

Baudet, S, Another activity for the cardiac biologist: ANKRD1 fishing. *Cardiovasc Res* 59: 529-31, 2003.

Chu, W, et al., Identification and characterization of a novel cytokine-inducible nuclear protein from human endothelial cells. *J Biol Chem* 270:10236-45, 1995.

Guminski, A D, Balleine, R L, Chiew, Y-E, Webster, L R, Tapner, M, Farrell, G, Harnett, P R, and deFazio, A, MRP2 (ABCC2) expression and cisplatin sensitivity in hepatocytes and human ovarian carcinoma. *Gynecol. Oncol.* 2005 [Epub ahead of print].

Jeyaseelan, R. et al. A novel cardiac-restricted target for doxorubicin. CARP, a nuclear modulator of gene expression in cardiac progenitor cells and cardiomyocytes. *J Biol Chem* 272(369): 22800-08. 1997

Kojic, S. et al., The Ankrd2 protein, a link between the sarcomere and the nucleus in skeletal muscle. *J Mol Biol* 339: 313-325, 2004.

Kricker, A, Ovarian cancer in Australian women. National Ovarian Cancer Program. National Breast Cancer Centre 2002.

Miller, M. K. et al., The muscle ankyrin repeat proteins: CARP, ankrd2/Arpp and DARP as a family of titin filament-based stress response modulators. *J Mol Biol* 333: 951-964, 2003.

Nakada, C, et al., Cardiac-restricted ankyrin-repeated protein is differentially induced in duchenne and congenital muscular dystrophy. *Lab Invest* 83: 711-9, 2003.

Niedner, H, et al., Identification of genes that mediate sensitivity to cisplatin. *Mol Pharmacol* 60:1153-60, 2001.

Robson, C, et al Isolation and characterization of Chinese hamster ovary cell lines sensitive to mitomycin C and bleomycin. Cancer Res 45: 5304-9, 1985.

Sambrook, J., et al. Molecular Cloning—A Laboratory Manual, 2nd Edition. Cold Spring Habour Laboratory Press, New York, USA. 1989.

Segelov, E., Mann, G., deFazio, A. and Harnett, P. R. Mechanisms determining sensitivity to cisplatin in three mutant Chinese hamster ovary cell lines. *Mut. Res.* 407(3): 243-52, 1998.

Taniguchi, T, et al., Disruption of the Fanconi anemia-BRCA pathway in cisplatin-sensitive ovarian tumors. *Nature Med* 9: 568-74, 2003.

Zou, Y, et al., ANKRD1, a cardiac ankyrin repeat protein, is downstream in the Nkx2-5 homeobox gene pathway. *Development* 124: 793-804, 1997.

The invention claimed is:

1. A method for increasing sensitivity of a tumor cell to one or more chemotherapeutic agents, the method comprising administering to the tumor cell an effective amount of an antagonist of a muscle ankyrin repeat protein, wherein the antagonist comprises an inhibitor of muscle ankyrin repeat protein expression that is a nucleic acid-based inhibitor.

2. The method of claim 1 wherein the nucleic acid-based inhibitor is an siRNA molecule or an antisense construct.

3. The method of claim 2 wherein the nucleic acid-based inhibitor is an siRNA molecule.

4. The method of claim 1 wherein the muscle ankyrin repeat protein is ANKRD1.

5. The method of claim 3 wherein the siRNA molecule comprises a nucleotide sequence having at least 80% sequence identity to a polynucleotide sequence as set forth in any one of SEQ ID NOs:5, 6 or 7, or a dsRNA corresponding thereto.

6. The method of claim 1, wherein the chemotherapeutic agent is a platinum-based chemotherapeutic agent.

7. A method for substantially inhibiting expression of a muscle ankyrin repeat protein in tumor cells, comprising introducing into the tumor cells an effective amount of an antagonist of the muscle ankyrin repeat protein wherein the antagonist comprises an inhibitor of muscle ankyrin repeat protein expression that is a nucleic acid-based inhibitor.

8. The method of claim 7, wherein the muscle ankyrin repeat protein is ANKRD1.

9. A method for substantially inhibiting expression of a muscle ankyrin repeat protein in tumor cells, comprising introducing into the tumor cells an effective amount of an inhibitory nucleic acid construct, said inhibitory nucleic acid construct comprising at least one of (a) a nucleotide sequence specific to at least a portion of a polynucleotide encoding a muscle ankyrin repeat protein, and (b) a nucleotide sequence specific to at least a portion of a regulatory region of a gene encoding the muscle ankyrin repeat protein of (a), wherein the inhibitory nucleic acid construct substantially inhibits expression of the muscle ankyrin repeat protein in tumor cells.

10. A method for increasing sensitivity of tumor cells to one or more chemotherapeutic agents, comprising introducing into the tumor cells an effective amount of an inhibitory nucleic acid construct, said inhibitory nucleic acid construct comprising at least one of (a) a nucleotide sequence specific to at least a portion of a polynucleotide encoding a muscle ankyrin repeat protein, and (b) a nucleotide sequence specific to at least a portion of a regulatory region of a gene encoding the muscle ankyrin repeat protein of (a), wherein the inhibitory nucleic acid construct substantially inhibits expression of the muscle ankyrin repeat protein in tumor cells.

11. The method of claim 6, wherein the platinum-based chemotherapeutic agent is selected from cisplatin, carboplatin and oxaliplatin.

12. The method of claim 7 wherein the nucleic acid-based inhibitor is an siRNA molecule or an antisense construct.

13. The method of claim 12 wherein the nucleic acid-based inhibitor is an siRNA molecule.

14. The method of claim 13 wherein the siRNA molecule comprises a nucleotide sequence having at least 80% sequence identity to a polynucleotide sequence as set forth in any one of SEQ ID NOs:5, 6 or 7, or a dsRNA corresponding thereto.

* * * * *

SEQUENCE LISTING

<160> NUMBER OF SEQ ID NOS: 21

<210> SEQ ID NO 1
<211> LENGTH: 319
<212> TYPE: PRT
<213> ORGANISM: Homo sapiens

<400> SEQUENCE: 1

```
Met Met Val Leu Lys Val Glu Glu Leu Val Thr Gly Lys Lys Asn Gly
 1               5                  10                  15

Asn Gly Glu Ala Gly Glu Phe Leu Pro Glu Asp Phe Arg Asp Gly Glu
            20                  25                  30

Tyr Glu Ala Ala Val Thr Leu Glu Lys Gln Glu Asp Leu Lys Thr Leu
        35                  40                  45

Leu Ala His Pro Val Thr Leu Gly Glu Gln Gln Trp Lys Ser Glu Lys
    50                  55                  60

Gln Arg Glu Ala Glu Leu Lys Lys Lys Leu Glu Gln Arg Ser Lys
65                  70                  75                  80

Leu Glu Asn Leu Glu Asp Leu Glu Ile Ile Ile Gln Leu Lys Lys Arg
                85                  90                  95

Lys Lys Tyr Arg Lys Thr Lys Val Pro Val Val Lys Glu Pro Glu Pro
            100                 105                 110

Glu Ile Ile Thr Glu Pro Val Asp Val Pro Thr Phe Leu Lys Ala Ala
        115                 120                 125
```

```
Leu Glu Asn Lys Leu Pro Val Val Glu Lys Phe Leu Ser Asp Lys Asn
            130                 135                 140

Asn Pro Asp Val Cys Asp Glu Tyr Lys Arg Thr Ala Leu His Arg Ala
145                 150                 155                 160

Cys Leu Glu Gly His Leu Ala Ile Val Glu Lys Leu Met Glu Ala Gly
                165                 170                 175

Ala Gln Ile Glu Phe Arg Asp Met Leu Glu Ser Thr Ala Ile His Trp
            180                 185                 190

Ala Ser Arg Gly Gly Asn Leu Asp Val Leu Lys Leu Leu Asn Lys
        195                 200                 205

Gly Ala Lys Ile Ser Ala Arg Asp Lys Leu Leu Ser Thr Ala Leu His
        210                 215                 220

Val Ala Val Arg Thr Gly His Tyr Glu Cys Ala Glu His Leu Ile Ala
225                 230                 235                 240

Cys Glu Ala Asp Leu Asn Ala Lys Asp Arg Glu Gly Asp Thr Pro Leu
                245                 250                 255

His Asp Ala Val Arg Leu Asn Arg Tyr Lys Met Ile Arg Leu Leu Ile
                260                 265                 270

Met Tyr Gly Ala Asp Leu Asn Ile Lys Asn Cys Ala Gly Lys Thr Pro
            275                 280                 285

Met Asp Leu Val Leu His Trp Gln Asn Gly Thr Lys Ala Ile Phe Asp
290                 295                 300

Ser Leu Arg Glu Asn Ser Tyr Lys Thr Ser Arg Ile Ala Thr Phe
305                 310                 315

<210> SEQ ID NO 2
<211> LENGTH: 960
<212> TYPE: DNA
<213> ORGANISM: Homo sapiens

<400> SEQUENCE: 2
atgatggtac tgaaagtaga ggaactggtc actggaaaga agaatggcaa tggggaggca      60
ggggaattcc ttcctgagga tttcagagat ggagagtatg aagctgctgt tactttagag     120
aagcaggagg atctgaagac acttctagcc caccctgtga ccctggggga gcaacagtgg     180
aaaagcgaga acaacgaga ggcagagctc aaaaagaaaa aactagaaca agatcaaag      240 cttgaaaatt tagaagacct tgaaataatc attcaactga agaaaggaa aaatacagg       300 aaaactaaag ttccagttgt aaaggaacca gaacctgaaa tcattacgga acctgtggat     360
gtgcctacgt ttctgaaggc tgctctggag aataaactgc cagtagtaga aaaattcttg     420
tcagacaaga caatccaga tgtttgtgat gagtataaac ggacagctct tcatagagca     480
tgcttggaag acatttggc aattgtggag aagttaatgg aagctggagc ccagatcgaa     540
ttccgtgata tgcttgaatc cacagccatc cactgggcaa gccgtggagg aaacctggat     600
gttttaaaat tgttgctgaa taaggagca aaaattagcg cccgagataa gttgctcagc      660
acagcgctgc atgtggcggt gaggactggc cactatgagt gcgcggagca tcttatcgcc     720
tgtgaggcag acctcaacgc caagacaga gaaggagata ccccgttgca tgatgcggtg     780
agactgaacc gctataagat gatccgactc tgattatgt atggcgcgga tctcaacatc     840
aagaactgtg ctgggaagac gccgatggat ctggtgctac actggcagaa tggaaccaaa     900
gcaatattcg acagcctcag agagaactcc tacaagacct ctcgcatagc tacattctga     960

<210> SEQ ID NO 3
<211> LENGTH: 319
```

<212> TYPE: PRT
<213> ORGANISM: Cricetulus griseus

<400> SEQUENCE: 3

```
Met Met Val Leu Arg Val Glu Glu Pro Val Thr Gly Lys Lys Asn Ser
  1               5                  10                  15

Ser Gly Ala Ala Gly Glu Phe Leu Ser Gly Asp Phe Arg Asp Gly Glu
             20                  25                  30

Tyr Glu Ala Ala Ile Ala Leu Glu Lys Gln Glu Asp Leu Lys Thr Leu
         35                  40                  45

Pro Val His His Val Asn Pro Glu Glu Gln Trp Lys Ser Glu Lys
     50                  55                  60

Gln Arg Glu Ala Glu Leu Lys Lys Lys Leu Glu Gln Arg Ser Lys
 65             70                  75                  80

Leu Glu Asn Leu Glu Asp Leu Glu Ile Ile Val Gln Leu Lys Lys Arg
                 85                  90                  95

Lys Lys Tyr Lys Lys Thr Lys Val Pro Val Val Lys Glu Pro Glu Pro
            100                 105                 110

Glu Ile Ile Thr Glu Pro Val Asp Val Pro Arg Phe Leu Lys Ala Ala
        115                 120                 125

Leu Glu Asn Lys Leu Pro Val Val Glu Lys Phe Leu Ser Asp Lys Asn
130                 135                 140

Ser Pro Asp Val Cys Asp Glu Tyr Lys Arg Thr Ala Leu His Arg Ala
145                 150                 155                 160

Cys Leu Glu Gly His Leu Ala Ile Val Glu Lys Leu Met Glu Ala Gly
                165                 170                 175

Ala Gln Ile Glu Phe Arg Asp Met Leu Glu Ser Thr Ala Ile His Trp
            180                 185                 190

Ala Cys Arg Gly Gly Asn Leu Asp Val Leu Lys Leu Leu Asn Lys
        195                 200                 205

Gly Ala Lys Ile Ser Ala Arg Asp Lys Leu Leu Ser Thr Ala Leu His
    210                 215                 220

Val Ala Val Arg Thr Gly His Tyr Glu Cys Ala Glu His Leu Ile Ala
225                 230                 235                 240

Cys Glu Ala Asp Leu Asn Ala Lys Asp Arg Glu Gly Asp Thr Pro Leu
                245                 250                 255

His Asp Ala Val Arg Leu Asn Arg Tyr Lys Met Ile Arg Leu Leu Met
            260                 265                 270

Thr Phe Gly Ala Asp Leu Asn Thr Lys Asn Cys Ala Gly Lys Thr Pro
        275                 280                 285

Met Asp Leu Val Leu His Trp Gln Asn Gly Thr Lys Ala Ile Phe Asp
290                 295                 300

Ser Leu Lys Glu Asn Gly Tyr Lys Thr Ser Arg Ile Ala Thr Phe
305                 310                 315
```

<210> SEQ ID NO 4
<211> LENGTH: 960
<212> TYPE: DNA
<213> ORGANISM: Cricetulus griseus

<400> SEQUENCE: 4

```
atgatggtgc tgagagtaga ggagccggta acagggaaga agaatagcag tggggccgca    60
ggggaattcc tttctgggga tttcagagat ggagaatatg aagctgccat tgctttggag   120
aaacaagagg atttgaagac tcttccagtc caccatgtga acccagagga gcaacaatgg   180
aaaagtgaga acagcgaga ggcagagctc aaaaagaaaa aattagaaca aagatcaaag   240
```

```
cttgaaaact tggaagacct tgaaataatt gttcaactga agaaaagaaa aaaatacaag    300
aagactaaag ttccagttgt gaaggaacca gaacctgaaa ttattactga acctgtggat    360
gtgccgaggt ttctgaaagc tgcgctggag aacaaactgc cagttgtaga gaaatttctg    420
tccgacaaga acagccccga tgtctgcgat gagtataaac ggaccgctct ccacagagca    480
tgcctagaag gacacttggc aattgtggag aagttaatgg aggctggagc ccagattgaa    540
ttccgtgata tgcttgaatc cacagccatc cactgggcat gtcgtggagg aaacctggat    600
gtcctgaaac tgttgttgaa caaaggggcc aaaatcagtg cccgagacaa gctgctcagc    660
acagcgctgc acgtggcggt gaggactggt cactacgagt gtgcagagca tctcatcgcc    720
tgtgaggcgg atctcaatgc caaggacaga gaaggagata ccccactgca cgacgctgtg    780
aggctgaatc gctataagat gattcggctc ttaatgacct tcgggcaga cctcaacacc    840 aagaactgtg ctgggaagac ccccatggac ctggtactgc actggcagaa tggaaccaaa    900
gcaatattcg cacagcctga agagaatggc tacaaaacct ctcgcatagc tacattctaa    960

<210> SEQ ID NO 5
<211> LENGTH: 64
<212> TYPE: DNA
<213> ORGANISM: Artificial Sequence
<220> FEATURE:
<223> OTHER INFORMATION: siRNA41

<400> SEQUENCE: 5
gatcccagtt ccagttgtga aggaattcaa gagattcctt cacaactgga acttttttg     60 gaaa                                                                 64

<210> SEQ ID NO 6
<211> LENGTH: 64
<212> TYPE: DNA
<213> ORGANISM: Artificial Sequence
<220> FEATURE:
<223> OTHER INFORMATION: siRNA58

<400> SEQUENCE: 6
gatcccgttc cgtgatatgc ttgaatttca agagaattca agcatatcac ggaattttt     60 ggaa                                                                 64

<210> SEQ ID NO 7
<211> LENGTH: 65
<212> TYPE: DNA
<213> ORGANISM: Artificial Sequence
<220> FEATURE:
<223> OTHER INFORMATION: siRNA77

<400> SEQUENCE: 7
gatcccgtgg aaccaaagca atattcttca agagagaata ttgctttggt tccatttttt    60
ggaaa                                                                65

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide probe

<400> SEQUENCE: 8
gtccaggggt tcagccacaa                                                20
```

```
<210> SEQ ID NO 9
<211> LENGTH: 24
<212> TYPE: DNA
<213> ORGANISM: Artificial Sequence
<220> FEATURE:
<223> OTHER INFORMATION: Oligonucleotide probe

<400> SEQUENCE: 9
acggtatctg atcgtcttcg aacc                                           24

<210> SEQ ID NO 10
<211> LENGTH: 30
<212> TYPE: DNA
<213> ORGANISM: Artificial Sequence
<220> FEATURE:
<223> OTHER INFORMATION: Primer

<400> SEQUENCE: 10
aacatgatgg tgctgagagt agaggagccg                                     30

<210> SEQ ID NO 11
<211> LENGTH: 28
<212> TYPE: DNA
<213> ORGANISM: Artificial Sequence
<220> FEATURE:
<223> OTHER INFORMATION: Primer

<400> SEQUENCE: 11
gcaccatcat gttggcagca gtgagtct                                       28

<210> SEQ ID NO 12
<211> LENGTH: 26
<212> TYPE: DNA
<213> ORGANISM: Artificial Sequence
<220> FEATURE:
<223> OTHER INFORMATION: Primer

<400> SEQUENCE: 12
tgcgctggag aacaaactgc cagttg                                         26

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
gaaccttcgg cacatccaca ggtc                                           24

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
agaaacagcg agaggcagag c                                              21

<210> SEQ ID NO 15
<211> LENGTH: 319
<212> TYPE: PRT
<213> ORGANISM: Cricetulus griseus

<400> SEQUENCE: 15

Met Met Val Leu Arg Val Glu Glu Pro Val Thr Gly Lys Lys Asn Ser
```

```
                1               5                  10                 15
Ser Gly Ala Ala Gly Glu Phe Leu Ser Gly Asp Phe Arg Asp Gly Glu
                        20                 25                 30

Tyr Glu Ala Ala Ile Ala Leu Glu Lys Gln Glu Asp Leu Lys Thr Leu
                35                 40                 45

Pro Val His His Val Asn Pro Glu Glu Gln Gln Trp Lys Ser Glu Lys
    50                 55                 60

Gln Arg Glu Ala Glu Leu Lys Lys Lys Leu Glu Gln Arg Ser Lys
65                  70                 75                 80

Leu Glu Asn Leu Glu Asp Leu Glu Ile Ile Val Gln Leu Lys Lys Arg
                    85                 90                 95

Lys Lys Tyr Lys Lys Thr Lys Val Pro Val Lys Glu Pro Glu Pro
                100                105                110

Glu Ile Ile Thr Glu Pro Val Asp Val Pro Arg Phe Leu Lys Ala Ala
                115                120                125

Leu Glu Asn Lys Leu Pro Val Val Glu Lys Phe Leu Ser Asp Lys Asn
                130                135                140

Ser Pro Asp Val Cys Asp Glu Tyr Lys Arg Thr Ala Leu His Arg Ala
145                 150                155                160

Cys Leu Glu Gly His Leu Ala Ile Val Glu Lys Leu Met Glu Ala Gly
                    165                170                175

Ala Gln Ile Glu Phe Arg Asp Met Leu Glu Ser Thr Ala Ile His Trp
                180                185                190

Ala Cys Arg Gly Gly Asn Leu Asp Val Leu Lys Leu Leu Asn Lys
                195                200                205

Gly Ala Lys Ile Ser Ala Arg Asp Lys Leu Leu Ser Thr Ala Leu His
                210                215                220

Val Ala Val Arg Thr Gly His Tyr Glu Cys Ala Glu His Leu Ile Ala
225                 230                235                240

Cys Glu Ala Asp Leu Asn Ala Lys Asp Arg Glu Gly Asp Thr Pro Leu
                245                250                255

His Asp Ala Val Arg Leu Asn Arg Tyr Lys Met Ile Arg Leu Leu Met
                260                265                270

Thr Phe Gly Ala Asp Leu Asn Thr Lys Asn Cys Ala Gly Lys Thr Pro
                275                280                285

Met Asp Leu Val Leu His Trp Gln Asn Gly Thr Lys Ala Ile Phe Asp
                290                295                300

Ser Leu Lys Glu Asn Gly Tyr Lys Thr Ser Arg Ile Ala Thr Phe
305                 310                315

<210> SEQ ID NO 16
<211> LENGTH: 319
<212> TYPE: PRT
<213> ORGANISM: Gallus gallus

<400> SEQUENCE: 16

Met Met Thr Met Lys Val Glu Glu Leu Val Thr Gly Lys Lys Thr Asp
1               5                  10                 15

Asp Lys Glu Ser Gly Ser Phe Leu Pro Glu Asp Phe Lys Thr Gly Glu
                    20                 25                 30

Tyr Glu Ala Ala Val Lys Leu Glu Lys Gln Asp Asp Leu Arg Thr Ala
                35                 40                 45

Ser Asp His Leu Ser Thr Gln Val Asp Met Ala His Gly Lys Glu Lys
                50                 55                 60

Lys Arg Glu Ala Glu Leu Lys Lys Lys Lys Leu Gln Glu Arg Ser Lys
```

```
                65                  70                  75                  80
Leu Glu Ser Leu Glu Asp Leu Glu Lys Ile Ile Gln Leu Lys Lys Lys
                    85                  90                  95

Lys Lys Cys Arg Lys Val Lys Ala Pro Leu Leu Lys Glu Pro Glu Pro
            100                 105                 110

Glu Val Ile Thr Gly Pro Val Asp Ile Ala Met Phe Phe Arg Ala Ala
        115                 120                 125

Leu Glu Asn Lys Leu Pro Val Ile Glu Lys Tyr Leu Ser Asp Lys Gly
    130                 135                 140

Asp Pro Asn Val Cys Asn Glu Tyr Lys Arg Thr Ala Leu His Arg Ala
145                 150                 155                 160

Cys Ser Glu Gly His Leu Glu Val Val Lys Leu Val Glu Ala Gly
                165                 170                 175

Ala Leu Leu Glu Leu Lys Asp Met Leu Glu Ser Thr Ala Leu His Trp
            180                 185                 190

Ala Cys Arg Gly Gly Asn Leu Glu Ile Val Lys Phe Leu Leu Asp Lys
        195                 200                 205

Gly Ile Asn Arg Asn Ala Arg Asp Lys Leu Arg Ser Thr Pro Leu His
    210                 215                 220

Val Ala Val Arg Thr Gly Gln His Asp Cys Ala Glu His Leu Ile Ala
225                 230                 235                 240

Cys Glu Ala Asp Leu Asn Ala Lys Asp Arg Glu Gly Asp Thr Pro Met
                245                 250                 255

His Asp Ala Val Arg Leu Asn Arg Tyr Lys Met Val Arg Leu Leu Ile
            260                 265                 270

Leu Tyr Gly Ala Asp Leu Thr Ile Lys Asn Val Asp Gly Lys Thr Pro
        275                 280                 285

Met Asp Leu Val Leu Gln Trp Gln Asn Gly Thr Lys Glu Leu Phe Asn
    290                 295                 300

Asn Leu Lys Asn Asn Ser Tyr Lys Ser Ala His Leu Asn Lys Phe
305                 310                 315

<210> SEQ ID NO 17
<211> LENGTH: 319
<212> TYPE: PRT
<213> ORGANISM: Homo sapiens

<400> SEQUENCE: 17

Met Met Val Leu Lys Val Glu Glu Leu Val Thr Gly Lys Lys Asn Gly
  1               5                  10                  15

Asn Gly Glu Ala Gly Glu Phe Leu Pro Glu Asp Phe Arg Asp Gly Glu
            20                  25                  30

Tyr Glu Ala Ala Val Thr Leu Glu Lys Gln Glu Asp Leu Lys Thr Leu
        35                  40                  45

Leu Ala His Pro Val Thr Leu Gly Glu Gln Trp Lys Ser Glu Lys
    50                  55                  60

Gln Arg Glu Ala Glu Leu Pro Lys Lys Leu Glu Gln Arg Ser Lys
65                  70                  75                  80

Leu Glu Asn Leu Glu Asp Leu Glu Ile Ile Gln Leu Lys Lys Arg
                85                  90                  95

Lys Lys Tyr Arg Lys Thr Lys Val Pro Val Lys Glu Pro Glu Pro
            100                 105                 110

Glu Ile Ile Thr Glu Pro Val Asp Val Pro Thr Phe Leu Lys Ala Ala
        115                 120                 125

Leu Glu Asn Lys Leu Pro Val Val Glu Lys Phe Leu Ser Asp Lys Asn
```

```
                130               135               140
Asn Pro Asp Val Cys Asp Glu Tyr Lys Arg Thr Ala Leu His Arg Ala
145                 150                 155                 160

Cys Leu Glu Gly His Leu Ala Ile Val Glu Lys Leu Met Glu Ala Gly
                165                 170                 175

Ala Gln Ile Glu Phe Arg Asp Met Leu Glu Ser Thr Ala Ile His Trp
            180                 185                 190

Ala Ser Arg Gly Gly Asn Leu Asp Val Leu Lys Leu Leu Leu Asn Lys
                195                 200                 205

Gly Ala Lys Ile Ser Ala Arg Asp Lys Leu Leu Ser Thr Ala Leu His
210                 215                 220

Val Ala Val Arg Thr Gly His Tyr Glu Cys Ala Glu His Leu Ile Ala
225                 230                 235                 240

Cys Glu Ala Asp Leu Asn Ala Lys Asp Arg Glu Gly Asp Thr Pro Leu
                245                 250                 255

His Asp Ala Val Arg Leu Asn Arg Tyr Lys Met Ile Arg Leu Leu Ile
                260                 265                 270

Met Tyr Gly Ala Asp Leu Asn Ile Lys Asn Cys Ala Gly Lys Thr Pro
            275                 280                 285

Met Asp Leu Val Leu His Trp Gln Asn Gly Thr Lys Ala Ile Phe Asp
290                 295                 300

Ser Leu Arg Glu Asn Ser Tyr Lys Thr Ser Arg Ile Ala Thr Phe
305                 310                 315

<210> SEQ ID NO 18
<211> LENGTH: 319
<212> TYPE: PRT
<213> ORGANISM: Sus scrofa

<400> SEQUENCE: 18

Met Met Val Leu Lys Val Glu Glu Leu Val Thr Gly Lys Lys Asn Gly
1               5                   10                  15

Gly Gly Asp Ala Gly Glu Phe Leu Pro Glu Asp Phe Arg Asp Gly Glu
                20                  25                  30

Tyr Glu Ala Ala Val Thr Leu Glu Lys Gln Glu Asp Leu Lys Thr Leu
            35                  40                  45

Pro Ala His Phe Val Ser Leu Gly Glu Gln Gln Trp Lys Ile Glu Lys
50                  55                  60

Glu Arg Glu Ala Glu Leu Lys Lys Lys Leu Glu Gln Arg Ser Lys
65                  70                  75                  80

Leu Glu Asn Leu Glu Asp Leu Glu Ile Ile Ile Gln Leu Lys Lys Arg
                85                  90                  95

Lys Lys Tyr Arg Lys Thr Lys Val Pro Val Val Lys Glu Pro Glu Pro
            100                 105                 110

Glu Val Ile Thr Glu Pro Val Asp Val Pro Arg Phe Leu Lys Ala Ala
        115                 120                 125

Leu Glu Asn Lys Leu Pro Val Val Glu Lys Phe Leu Ser Asp Lys Asn
130                 135                 140

Asn Pro Asp Val Cys Asp Glu Tyr Lys Arg Thr Ala Leu His Arg Ala
145                 150                 155                 160

Cys Leu Glu Gly His Leu Ala Ile Val Glu Lys Leu Ile Glu Ala Gly
                165                 170                 175

Ala Gln Ile Glu Phe Arg Asp Met Leu Glu Ser Thr Ala Ile His Trp
            180                 185                 190

Ala Ser Arg Gly Gly Asn Leu Asp Val Leu Lys Leu Leu Leu Asn Lys
```

```
                195                 200                 205
Gly Ala Lys Ile Ser Ala Arg Asp Lys Leu Leu Ser Thr Ala Leu His
            210                 215                 220

Val Ala Val Arg Thr Gly His Tyr Glu Cys Ala Glu His Leu Ile Ala
225                 230                 235                 240

Cys Glu Ala Asp Leu Asn Ala Lys Asp Arg Glu Gly Asp Thr Pro Leu
                245                 250                 255

His Asp Ala Val Arg Leu Asn Arg Tyr Lys Met Ile Arg Leu Leu Ile
            260                 265                 270

Thr Tyr Gly Ala Asp Leu Asn Val Lys Asn Cys Ala Gly Lys Thr Pro
            275                 280                 285

Met Asp Leu Val Leu Asn Trp Gln Asn Gly Thr Lys Ala Ile Phe Asp
            290                 295                 300

Ser Leu Lys Glu Asn Ser Tyr Lys Ala Ser Arg Ile Ala Thr Phe
305                 310                 315

<210> SEQ ID NO 19
<211> LENGTH: 318
<212> TYPE: PRT
<213> ORGANISM: Oryctolagus cuniculus

<400> SEQUENCE: 19

Met Met Val Leu Lys Val Glu Glu Leu Val Thr Gly Lys Lys Ser Ser
  1               5                  10                  15

Asn Gly Glu Thr Gly Glu Phe Leu Pro Asp Asp Phe Arg Asp Gly Gln
             20                  25                  30

Tyr Glu Ala Ala Val Thr Ser Glu Lys Gln Glu Asp Leu Lys Thr Leu
         35                  40                  45

Pro Ala His His Val Ser Leu Ala Glu Gln Gln Trp Glu Arg Glu Lys
     50                  55                  60

Gln Leu Glu Ala Glu Leu Lys Lys Lys Leu Glu Gln Arg Ser Lys
 65                  70                  75                  80

Leu Glu Asn Leu Glu Asp Leu Glu Ile Ile Ile Gln Leu Lys Lys Arg
                 85                  90                  95

Lys Lys Tyr Arg Lys Thr Lys Val Pro Val Ala Lys Glu Pro Glu Pro
            100                 105                 110

Glu Ile Ile Thr Glu Pro Val Asp Val Pro Arg Phe Leu Lys Ala Ala
            115                 120                 125

Leu Glu Asn Lys Leu Ala Val Val Glu Lys Phe Leu Ser Asp Gln Asn
            130                 135                 140

Asn Pro Asp Val Cys Asp Glu Tyr Lys Arg Thr Ala Leu His Arg Ala
145                 150                 155                 160

Cys Leu Glu Gly His Leu Ala Ile Val Glu Leu Met Glu Ala Gly Ala
                165                 170                 175

Gln Ile Glu Phe Arg Asp Met Leu Glu Ser Thr Ala Ile His Trp Ala
            180                 185                 190

Cys Arg Gly Gly Asn Leu Glu Val Leu Lys Leu Leu Asn Lys Gly
            195                 200                 205

Ala Lys Ile Ser Ala Arg Asp Lys Leu Leu Ser Thr Ala Leu His Val
        210                 215                 220

Ala Val Arg Thr Gly His Tyr Glu Cys Ala Glu His Leu Ile Ala Cys
225                 230                 235                 240

Glu Ala Asp Leu Asn Ala Lys Asp Arg Glu Gly Asp Thr Pro Leu His
                245                 250                 255

Asp Ala Val Arg Leu Asn Arg Tyr Lys Met Ile Arg Leu Leu Ile Met
```

```
            260                 265                 270
Tyr Gly Ala Asp Leu Thr Ile Lys Asn Ser Ala Gly Lys Thr Pro Met
            275                 280                 285

Asp Leu Val Leu Asn Trp Gln Asn Gly Thr Lys Ala Ile Phe Asp Ser
            290                 295                 300

Leu Lys Glu Asn Ser Tyr Lys Thr Ser Arg Ile Ala Thr Phe
305                 310                 315

<210> SEQ ID NO 20
<211> LENGTH: 319
<212> TYPE: PRT
<213> ORGANISM: Rattus norvegicus

<400> SEQUENCE: 20

Met Met Val Phe Arg Val Glu Glu Leu Val Thr Gly Lys Lys Asn Ser
1               5                   10                  15

Asn Gly Ser Ser Gly Glu Phe Leu Pro Gly Glu Phe Arg Asn Gly Glu
            20                  25                  30

Tyr Glu Ala Ala Val Ala Leu Glu Lys Gln Glu Asp Leu Lys Thr Leu
            35                  40                  45

Pro Ala Asn Ser Val Asn Leu Gly Glu Glu Gln Arg Lys Ser Glu Lys
            50                  55                  60

Val Arg Glu Ala Glu Leu Lys Lys Lys Leu Glu Gln Arg Ser Lys
65                  70                  75                  80

Leu Glu Asn Leu Glu Asp Leu Glu Ile Ile Val Gln Leu Lys Lys Arg
                    85                  90                  95

Lys Lys Tyr Lys Lys Thr Lys Val Pro Val Val Lys Glu Pro Glu Pro
            100                 105                 110

Glu Ile Ile Thr Glu Pro Val Asp Val Pro Arg Phe Leu Lys Ala Ala
            115                 120                 125

Leu Glu Asn Lys Leu Pro Val Val Glu Lys Phe Leu Ser Asp Lys Asn
            130                 135                 140

Ser Pro Asp Val Cys Asp Glu Tyr Lys Arg Thr Ala Leu His Arg Ala
145                 150                 155                 160

Cys Leu Glu Gly His Leu Ala Ile Val Glu Lys Leu Met Glu Ala Gly
                    165                 170                 175

Ala Gln Ile Glu Phe Arg Asp Met Leu Glu Ser Thr Ala Ile His Trp
            180                 185                 190

Ala Cys Arg Gly Gly Asn Leu Asp Val Leu Lys Leu Leu Asn Lys
            195                 200                 205

Gly Ala Lys Ile Ser Ala Arg Asp Lys Leu Leu Ser Thr Ala Leu His
            210                 215                 220

Val Ala Val Arg Thr Gly His Tyr Glu Cys Ala Glu His Leu Ile Ala
225                 230                 235                 240

Cys Glu Ala Asp Leu Asn Ala Lys Asp Arg Glu Gly Asp Thr Pro Leu
                    245                 250                 255

His Asp Ala Val Arg Leu Asn Arg Tyr Lys Met Ile Arg Leu Leu Met
            260                 265                 270

Thr Phe Gly Ala Asp Leu Asn Val Lys Asn Cys Ala Gly Lys Ile Pro
            275                 280                 285

Met Asp Leu Val Leu His Trp Gln Asn Gly Thr Lys Ala Ile Phe Asp
            290                 295                 300

Ser Leu Lys Glu Asn Ala Tyr Lys Asn Ser Arg Ile Ala Thr Phe
305                 310                 315
```

-continued

```
<210> SEQ ID NO 21
<211> LENGTH: 319
<212> TYPE: PRT
<213> ORGANISM: Artificial Sequence
<220> FEATURE:
<223> OTHER INFORMATION: Consensus sequence of ANKRD1 gene product
<220> FEATURE:
<221> NAME/KEY: VARIANT
<222> LOCATION: 16
<223> OTHER INFORMATION: Xaa = Ser, Asp or Gly
<220> FEATURE:
<221> NAME/KEY: VARIANT
<222> LOCATION: 17
<223> OTHER INFORMATION: Xaa = Ser, Asp, Asn or Gly
<220> FEATURE:
<221> NAME/KEY: VARIANT
<222> LOCATION: 19
<223> OTHER INFORMATION: Xaa = Ala, Glu, Asp or Ser
<220> FEATURE:
<221> NAME/KEY: VARIANT
<222> LOCATION: 20
<223> OTHER INFORMATION: Xaa = Ala, Ser or Thr
<220> FEATURE:
<221> NAME/KEY: VARIANT
<222> LOCATION: 26
<223> OTHER INFORMATION: Xaa = Gly, Glu or Asp
<220> FEATURE:
<221> NAME/KEY: VARIANT
<222> LOCATION: (38)...(0)
<223> OTHER INFORMATION: Xaa = Ala, Lys or Thr
<220> FEATURE:
<221> NAME/KEY: VARIANT
<222> LOCATION: (52)...(0)
<223> OTHER INFORMATION: Xaa = His, Leu, Phe or Ser
<220> FEATURE:
<221> NAME/KEY: VARIANT
<222> LOCATION: (54)...(0)
<223> OTHER INFORMATION: Xaa = Asn, Thr or Ser
<220> FEATURE:
<221> NAME/KEY: VARIANT
<222> LOCATION: (56)...(0)
<223> OTHER INFORMATION: Xaa = Glu, Val, Gly or Ala
<220> FEATURE:
<221> NAME/KEY: VARIANT
<222> LOCATION: (62)...(0)
<223> OTHER INFORMATION: Xaa = Ser, Lys, Ile or Arg
<220> FEATURE:
<221> NAME/KEY: VARIANT
<222> LOCATION: (65)...(0)
<223> OTHER INFORMATION: Xaa = Gln, Lys, Glu or Val
<220> FEATURE:
<221> NAME/KEY: VARIANT
<222> LOCATION: (145)...(0)
<223> OTHER INFORMATION: Xaa = Ser, Asp or Asn
<220> FEATURE:
<221> NAME/KEY: VARIANT
<222> LOCATION: (273)...(0)
<223> OTHER INFORMATION: Xaa = Thr, Leu or Met
<220> FEATURE:
<221> NAME/KEY: VARIANT
<222> LOCATION: (280)...(0)
<223> OTHER INFORMATION: Xaa = Thr, Ile or Val
<220> FEATURE:
<221> NAME/KEY: VARIANT
<222> LOCATION: (294)...(0)
<223> OTHER INFORMATION: Xaa  = His, Gln or Asn
<220> FEATURE:
<221> NAME/KEY: VARIANT
<222> LOCATION: (313)...(0)
<223> OTHER INFORMATION: Xaa = Thr, Ser, Ala or Asn

<400> SEQUENCE: 21

Met Met Val Leu Lys Val Glu Glu Leu Val Thr Gly Lys Lys Asn Xaa
 1               5                   10                  15

Xaa Gly Xaa Xaa Gly Glu Phe Leu Pro Xaa Asp Phe Arg Asp Gly Glu
            20                  25                  30

Tyr Glu Ala Ala Val Xaa Leu Glu Lys Gln Glu Asp Leu Lys Thr Leu
```

-continued

```
                   35                    40                    45
Pro Ala His Xaa Val Xaa Leu Xaa Glu Gln Gln Trp Lys Xaa Glu Lys
    50                   55                       60

Xaa Arg Glu Ala Glu Leu Lys Lys Lys Leu Glu Gln Arg Ser Lys
65                  70                  75                  80

Leu Glu Asn Leu Glu Asp Leu Glu Ile Ile Ile Gln Leu Lys Lys Arg
                85                  90                  95

Lys Lys Tyr Arg Lys Thr Lys Val Pro Val Val Lys Glu Pro Glu Pro
            100                 105                 110

Glu Ile Ile Thr Glu Pro Val Asp Val Pro Arg Phe Leu Lys Ala Ala
            115                 120                 125

Leu Glu Asn Lys Leu Pro Val Val Glu Lys Phe Leu Ser Asp Lys Asn
                130                 135                 140

Xaa Pro Asp Val Cys Asp Glu Tyr Lys Arg Thr Ala Leu His Arg Ala
145                 150                 155                 160

Cys Leu Glu Gly His Leu Ala Ile Val Glu Lys Leu Met Glu Ala Gly
                165                 170                 175

Ala Gln Ile Glu Phe Arg Asp Met Leu Glu Ser Thr Ala Ile His Trp
            180                 185                 190

Ala Cys Arg Gly Gly Asn Leu Asp Val Leu Lys Leu Leu Leu Asn Lys
            195                 200                 205

Gly Ala Lys Ile Ser Ala Arg Asp Lys Leu Leu Ser Thr Ala Leu His
    210                 215                 220

Val Ala Val Arg Thr Gly His Tyr Glu Cys Ala Glu His Leu Ile Ala
225                 230                 235                 240

Cys Glu Ala Asp Leu Asn Ala Lys Asp Arg Glu Gly Asp Thr Pro Leu
                245                 250                 255

His Asp Ala Val Arg Leu Asn Arg Tyr Lys Met Ile Arg Leu Leu Ile
            260                 265                 270

Xaa Tyr Gly Ala Asp Leu Asn Xaa Lys Asn Cys Ala Gly Lys Thr Pro
    275                 280                 285

Met Asp Leu Val Leu Xaa Trp Gln Asn Gly Thr Lys Ala Ile Phe Asp
    290                 295                 300

Ser Leu Lys Glu Asn Ser Tyr Lys Xaa Ser Arg Ile Ala Thr Phe
305                 310                 315
```